US 9,125,588 B2

(12) United States Patent
Parks et al.

(10) Patent No.: US 9,125,588 B2
(45) Date of Patent: Sep. 8, 2015

(54) MICRO-REMOTE GASTROINTESTINAL PHYSIOLOGICAL MEASUREMENT DEVICE

(75) Inventors: Thomas R. Parks, Hermosa Beach, CA (US); Jae S. Son, Rancho Palos Verdes, CA (US)

(73) Assignee: Sierra Scientific Instruments, Inc.

( * ) Notice: Subject to any disclaimer, the term of this patent is extended or adjusted under 35 U.S.C. 154(b) by 1834 days.

(21) Appl. No.: 12/018,049

(22) Filed: Jan. 22, 2008

(65) Prior Publication Data

US 2008/0228047 A1    Sep. 18, 2008

Related U.S. Application Data

(60) Provisional application No. 60/881,439, filed on Jan. 19, 2007.

(51) Int. Cl.
*A61B 19/00* (2006.01)
*A61B 5/07* (2006.01)
*A61B 1/00* (2006.01)
(Continued)

(52) U.S. Cl.
CPC ............ *A61B 5/073* (2013.01); *A61B 1/00147* (2013.01); *A61B 1/233* (2013.01); *A61B 1/273* (2013.01); *A61B 5/0538* (2013.01); *A61B 5/14539* (2013.01); *A61B 5/42* (2013.01);
(Continued)

(58) Field of Classification Search
CPC .... A61B 1/00147; A61B 1/233; A61B 1/273; A61B 5/073; A61B 5/1451; A61B 5/42; A61B 1/041; A61B 5/0538; A61B 5/14539; A61B 5/14503; A61B 2560/063

USPC .............. 606/129, 1, 108; 600/102, 103, 104, 600/106, 109, 156; 604/21, 514, 59, 60, 70, 604/72
See application file for complete search history.

(56) References Cited

U.S. PATENT DOCUMENTS

| 3,528,429 A | 9/1970 | Beal et al. |
| 3,715,638 A | 2/1973 | Polye |

(Continued)

FOREIGN PATENT DOCUMENTS

| KR | 10-2008-0020281 A | 3/2008 |
| WO | WO 00/59376 | 10/2000 |

(Continued)

OTHER PUBLICATIONS

Hirano, Ikuo et al., "ACG Practice Guidelines: Esophageal Reflux Testing," *American Journal of Gastroenterology*, ISSN 0002-9270, (2007) pp. 668-685.

(Continued)

*Primary Examiner* — Katrina Stransky
(74) *Attorney, Agent, or Firm* — Wolf, Greenfield & Sacks, P.C.

(57) ABSTRACT

A physiological sensor-transmitter assembly for measuring a physiological property at an internal body location of a subject over time is described. An instrument for inserting the assembly in the subject and a method of monitoring a physiological property measured at the internal body location over time are also described. The assembly includes a sensor and a transmitter adapted to transmit information from the sensor in a non-wired fashion to a receiver. The assembly also includes an anchor adapted to attach to an externally accessible portion of a subject and a tether that connects the sensor and the anchor to maintain a position of the sensor within the gastrointestinal tract of the subject.

19 Claims, 15 Drawing Sheets

(51) Int. Cl.
*A61B 1/233* (2006.01)
*A61B 1/273* (2006.01)
*A61B 5/053* (2006.01)
*A61B 5/145* (2006.01)
*A61B 5/00* (2006.01)
*A61B 1/04* (2006.01)

(52) U.S. Cl.
CPC ............ *A61B1/041* (2013.01); *A61B 5/14503* (2013.01); *A61B 2560/063* (2013.01)

(56) References Cited

U.S. PATENT DOCUMENTS

| | | |
|---|---|---|
| 3,858,097 A | 12/1974 | Polye |
| 4,238,662 A | 12/1980 | Lao |
| 4,326,535 A | 4/1982 | Steffel et al. |
| 4,426,673 A | 1/1984 | Bell et al. |
| 4,434,203 A | 2/1984 | Briefer |
| 4,526,043 A | 7/1985 | Boie et al. |
| 4,542,436 A | 9/1985 | Carusillo |
| 4,561,450 A | 12/1985 | Bryant |
| 4,644,801 A | 2/1987 | Kustanovich |
| 4,827,763 A | 5/1989 | Bourland et al. |
| 4,839,512 A | 6/1989 | Speck |
| 4,862,743 A | 9/1989 | Seitz |
| 5,005,421 A | 4/1991 | Hegner |
| 5,070,735 A | 12/1991 | Reichert et al. |
| 5,117,827 A | 6/1992 | Stuebe et al. |
| 5,225,959 A | 7/1993 | Stearns |
| 5,525,280 A | 6/1996 | Shukla et al. |
| 5,533,515 A | 7/1996 | Coller et al. |
| 5,844,287 A | 12/1998 | Hassan et al. |
| 5,942,733 A | 8/1999 | Allen et al. |
| 5,965,821 A | 10/1999 | Grudzien |
| 5,983,727 A | 11/1999 | Wellman et al. |
| 5,984,860 A * | 11/1999 | Shan ........................ 600/116 |
| 6,060,756 A | 5/2000 | Machida et al. |
| 6,132,371 A | 10/2000 | Dempsey et al. |
| 6,248,655 B1 | 6/2001 | Machida et al. |
| 6,285,897 B1 | 9/2001 | Kilcoyne et al. |
| 6,293,907 B1 * | 9/2001 | Axon et al. .................... 600/114 |
| 6,310,371 B1 | 10/2001 | Hung |
| 6,402,689 B1 | 6/2002 | Scarantino et al. |
| 6,460,416 B1 | 10/2002 | Igel |
| 6,475,145 B1 | 11/2002 | Baylor |
| 6,518,083 B2 | 2/2003 | Sato et al. |
| 6,640,642 B1 | 11/2003 | Onose et al. |
| 6,689,056 B1 | 2/2004 | Kilcoyne et al. |
| 6,884,213 B2 * | 4/2005 | Raz et al. .................... 600/104 |
| 6,945,115 B1 | 9/2005 | Wang |
| 7,062,308 B1 | 6/2006 | Jackson |
| 7,076,305 B2 | 7/2006 | Imran et al. |
| 7,107,100 B2 | 9/2006 | Imran et al. |
| 7,118,531 B2 | 10/2006 | Krill |
| 7,120,498 B2 | 10/2006 | Imran et al. |
| 7,152,485 B2 | 12/2006 | Okada |
| 7,174,793 B2 | 2/2007 | Morimoto |
| 7,196,694 B2 | 3/2007 | Roberts |
| 7,207,941 B2 | 4/2007 | Sharf |
| 7,395,721 B2 | 7/2008 | Taniguchi |
| 7,398,587 B2 | 7/2008 | Morimoto |
| 2002/0035331 A1 | 3/2002 | Brockway et al. |
| 2002/0042562 A1 | 4/2002 | Meron et al. |
| 2002/0151770 A1 | 10/2002 | Noll, III et al. |
| 2003/0018280 A1 | 1/2003 | Lewkowicz et al. |
| 2003/0079547 A1 | 5/2003 | Baek |
| 2003/0094663 A1 | 5/2003 | Sato et al. |
| 2003/0107095 A1 | 6/2003 | Kurtz |
| 2003/0167024 A1 * | 9/2003 | Imran et al. .................... 601/15 |
| 2004/0046574 A1 | 3/2004 | Chou |
| 2004/0055396 A1 | 3/2004 | Morimoto |
| 2004/0058469 A1 | 3/2004 | Kowarz |
| 2004/0111019 A1 | 6/2004 | Long |
| 2004/0181155 A1 * | 9/2004 | Glukhovsky .................. 600/476 |
| 2004/0206190 A1 | 10/2004 | Kawahata |
| 2004/0215128 A1 * | 10/2004 | Eerdmans ........................ 604/27 |
| 2004/0219706 A1 | 11/2004 | Wan |
| 2005/0038370 A1 | 2/2005 | Kuth et al. |
| 2005/0043706 A1 * | 2/2005 | Eaton et al. .................... 604/500 |
| 2005/0068044 A1 | 3/2005 | Peine et al. |
| 2005/0085697 A1 | 4/2005 | Yokoi et al. |
| 2005/0148884 A1 | 7/2005 | Parks et al. |
| 2005/0182342 A1 | 8/2005 | Dinsmoor et al. |
| 2005/0208696 A1 | 9/2005 | Villa et al. |
| 2005/0226281 A1 | 10/2005 | Faraone et al. |
| 2005/0245795 A1 | 11/2005 | Goode, Jr. et al. |
| 2006/0004255 A1 | 1/2006 | Iddan et al. |
| 2006/0071286 A1 | 4/2006 | Axelrod et al. |
| 2006/0096384 A1 | 5/2006 | Harish et al. |
| 2006/0138574 A1 | 6/2006 | Saito et al. |
| 2006/0195014 A1 * | 8/2006 | Seibel et al. .................. 600/102 |
| 2006/0273417 A1 | 12/2006 | Ganapathi et al. |
| 2007/0225576 A1 | 9/2007 | Brown et al. |
| 2007/0299345 A1 | 12/2007 | Adachi et al. |
| 2008/0018608 A1 | 1/2008 | Serban et al. |
| 2008/0018611 A1 | 1/2008 | Serban et al. |
| 2008/0202251 A1 | 8/2008 | Serban et al. |
| 2009/0247992 A1 * | 10/2009 | Shalon et al. ...................... 606/1 |

FOREIGN PATENT DOCUMENTS

| | | |
|---|---|---|
| WO | WO 02/26103 A2 | 4/2002 |
| WO | WO 2007/007724 A1 | 1/2007 |

OTHER PUBLICATIONS

SmartPill GI Monitoring System Brochure from http://www.smartpillcorp.com/site/smartpill/assets/pdf/SmartPill_GI_Monitoring_System_Brochure.pdf, printed on May 9, 2008, 6 pages.
SmartPill Capsule Operational Specifications from http://www.smartpillcorp.com/site/smartpill/assets/pdf/SmartPill_Operational_Specs.pdf, printed on May 9, 2008, 1 page.
European Search Report issued on Nov. 23, 2011 for corresponding European Patent Application No. EP 08724647.
R.H. Colson et al., "An accurate, long-term, ph-sensitive radio pill for ingestion and implantation," *Biotelemetry Patient Monitoring*, vol. 8, No. 4, Jan. 1, 1981, pp. 213-227.

* cited by examiner

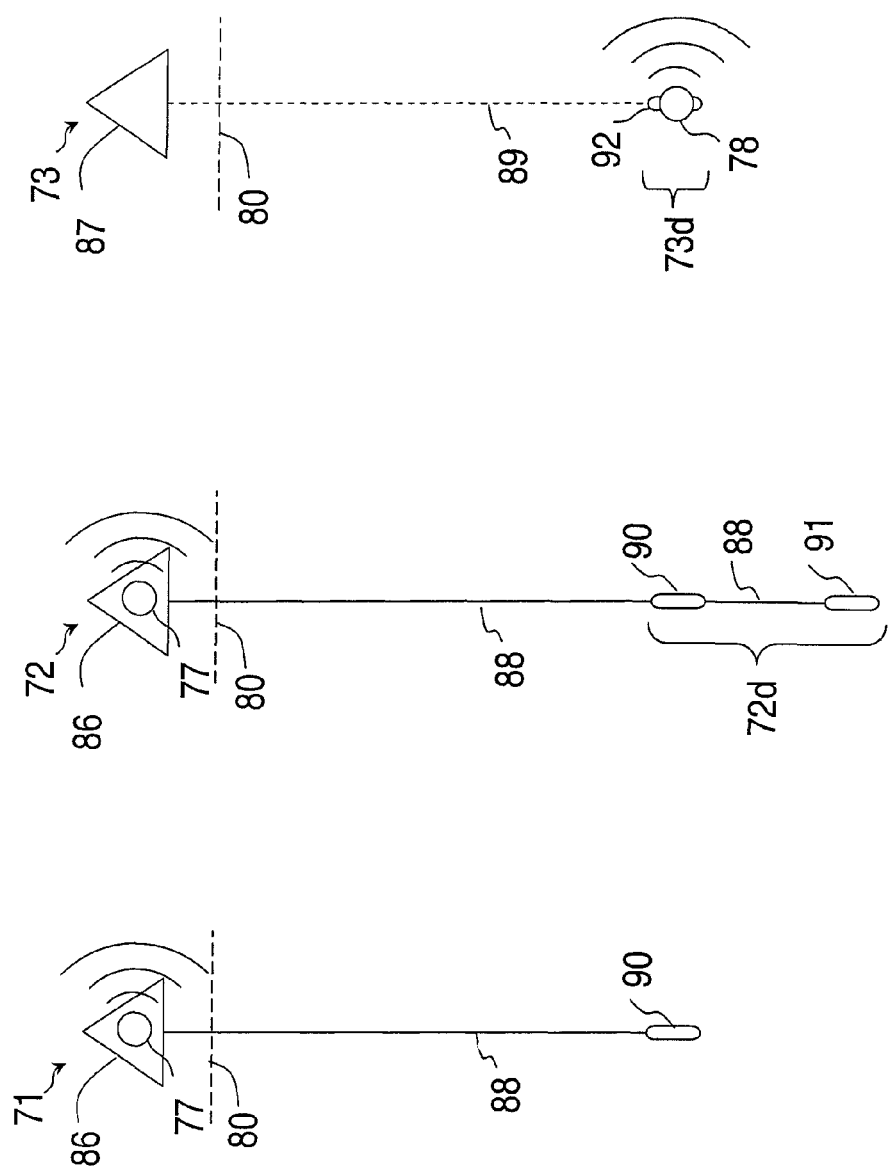

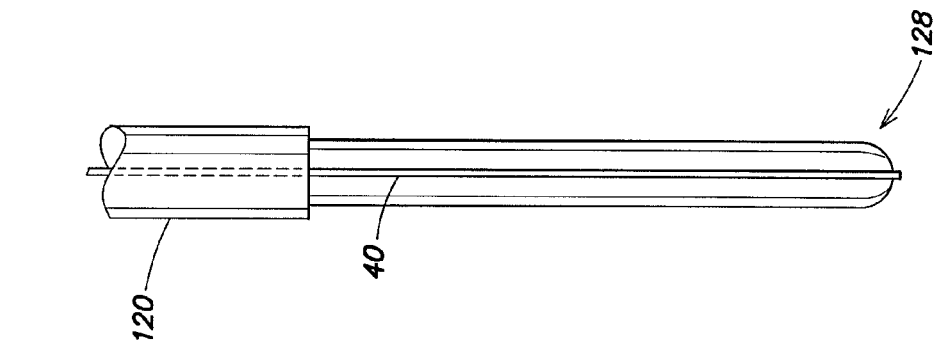
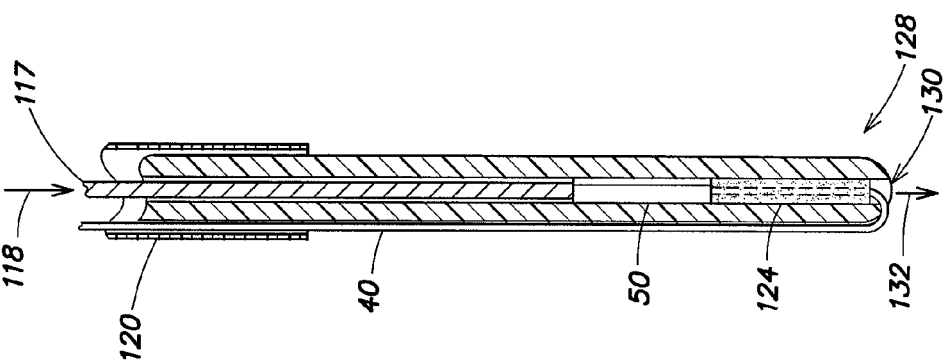
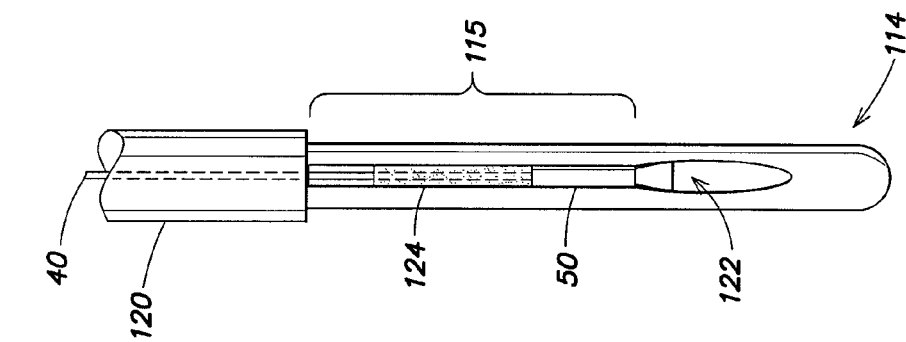
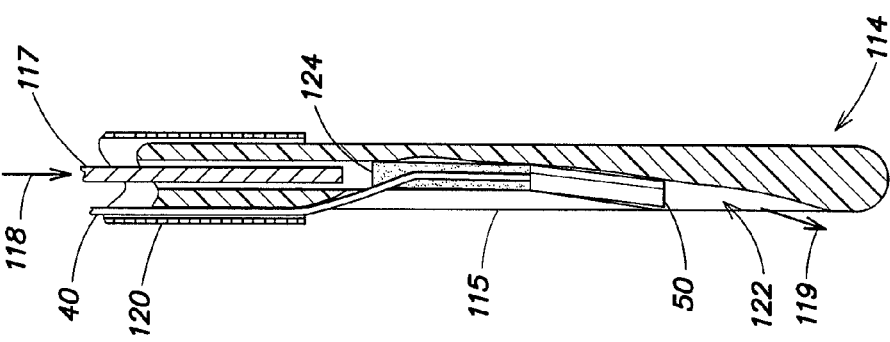

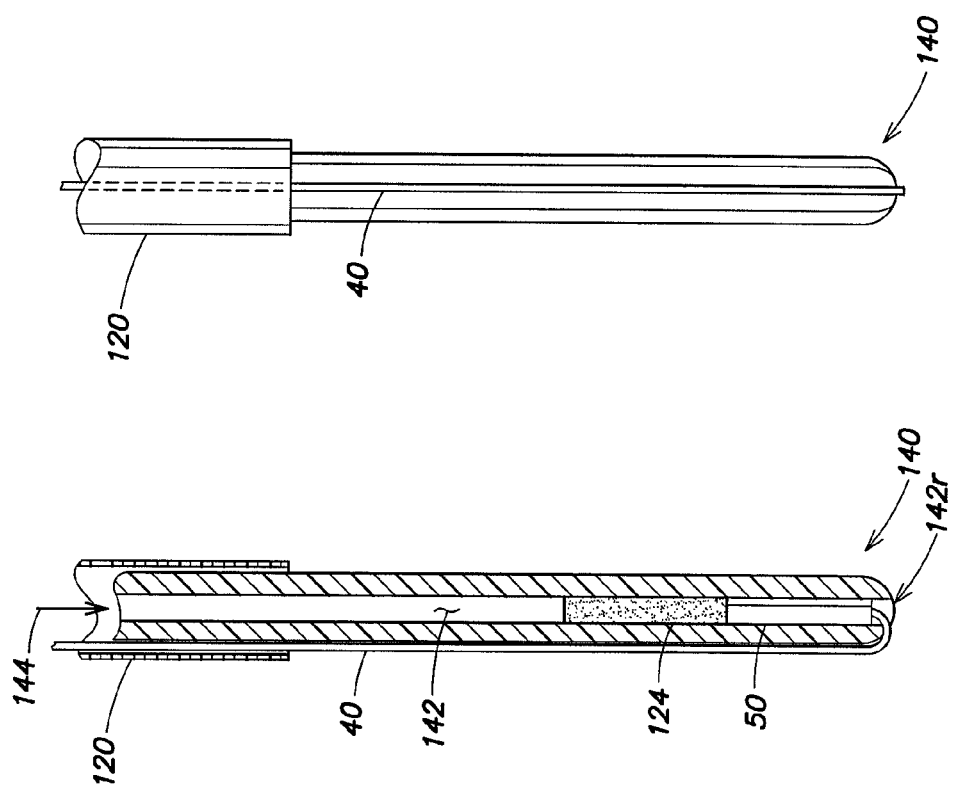
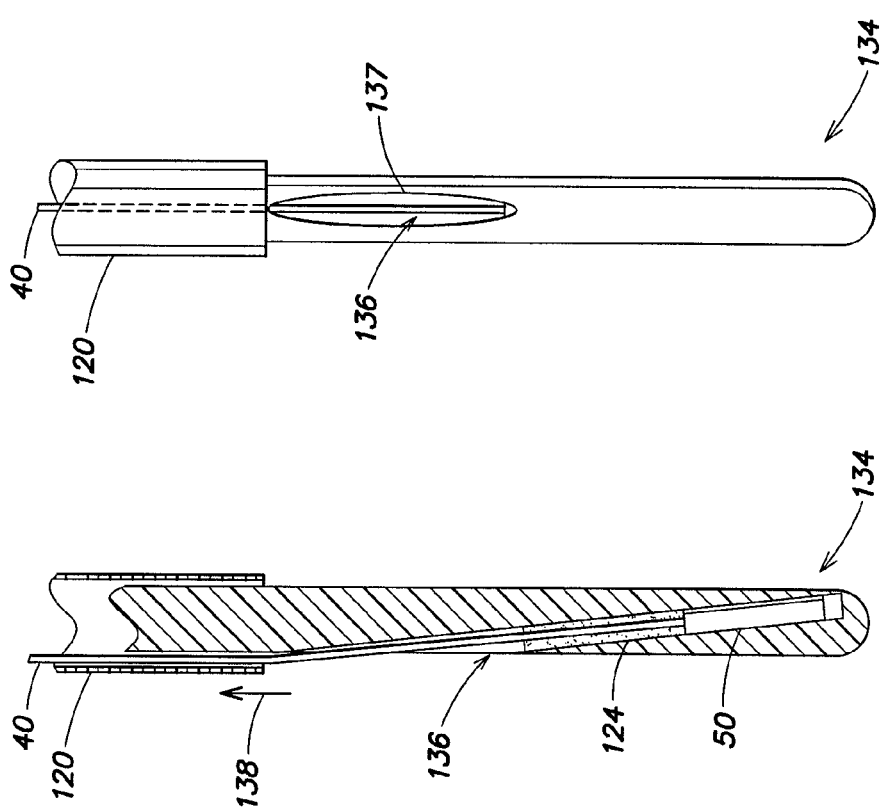

200b

Wirelessly receive a signal from the transmitter that includes information regarding values of a physiological property measured at the selected internal body location, *228*

↓

Record the received signal, *230*

↓

Transfer the recorded signal to an analysis and display device, *232*

↓

Analyze the received signal, *234*

↓

Display information from the received signal, *236*

↓

Withdraw, through the nasal-gastric segment, the sensor and the connected tether after receiving the signal for a determined period of time, *240*

*FIG. 14B*

MICRO-REMOTE GASTROINTESTINAL PHYSIOLOGICAL MEASUREMENT DEVICE

RELATED APPLICATIONS

This application claims the benefit under 35 U.S.C. §119 (e) to U.S. provisional patent application Ser. No. 60/881,439, entitled MICRO-REMOTE GASTROINTESTINAL PHYSIOLOGICAL MEASUREMENT DEVICE, filed on Jan. 19, 2007, the entirety of which is herein incorporated by reference.

FIELD OF USE

Embodiments of this invention are directed to an apparatus for measuring one or more physiological properties within a body of a subject.

BACKGROUND

Gastrointestinal monitoring systems measure one or more physiological properties at a location within the gastrointestinal (GI) tract of a subject. Systems that monitor reflux of gastric contents into the esophagus (gastroesophageal reflux) and also above the esophagus into the pharynx and larynx aid in diagnosis and treatment of various GI disorders and conditions, such as gastrointestinal reflux disease (GERD), heartburn, esophageal scarring (possibly accompanied by dysphagia), reflux esophagitis, Barrett's esophagus, laryngitis and chest pain. In physiological monitoring systems, values of physiological properties of interest (e.g. pH, pressure, temperature, etc.) are measured at a location within a body lumen or an organ of the subject, and information regarding the measured values is sent to a device external to the subject that receives the information and may record, analyze and/or transfer the information.

Some known upper GI (i.e. pharyngeal, esophageal, and gastric) pH measurement systems employ large diameter (typically ≥1.5 mm diameter) relatively stiff catheters that facilitate patient intubation. In such a system, a large diameter catheter is positioned with a detecting portion of the catheter within the patient and a proximal portion of the catheter exiting out through the patient's nose and extending to a remote data logging device, which is normally located at the patient's waist. The catheter remains within the patient throughout the monitoring process (typically about 24 hours), often causing pain and discomfort that may affect the patient's diet and ability to sleep and thereby negatively affect the degree to which collected data are representative of the true patient condition. Additionally, the patent may be self-conscious about the appearance of the catheter exiting the patient's nose and extending down the patient's neck, causing the patient to restrict his or her activities, such as work or other physical activities during monitoring.

Capsules that use micro-electronics and sensors have been developed for physiological measurements within the GI track (e.g. Smart Pill Diagnostics, Inc.). Such a remote sensing capsule wirelessly transmits physiological data (e.g. pH, temperature, pressure, etc.) measured at the capsule's current location as the capsule moves through the GI system. A known monitoring system including such a capsule may avoid the pain, discomfort and appearance issues associated with known catheter systems. However, the remote sensing capsules, which are swallowed, do not take measurements at a fixed location in the GI system over an extended period of time because a remote sensing capsule does not maintain a fixed location within the GI system and is carried along the GI tract over time.

One known method to fix an internal body location of a remote sensing capsule for measurements of esophageal pH is to tether the capsule to the patient's tooth. However, the tooth attachment method suffers from substantial drawbacks associated with operator difficulty with attachment of the tether to the tooth, and patient intolerance due to discomfort of the tether in the pallet including elicitation of the gag reflex.

Another method to fix an internal body location of a remote sensing capsule is implantation of an implantable remote sensing capsule within the GI tract of a subject (e.g. Bravo™, Medtronic, Minneapolis, Minn.). The remote sensing capsule may be implanted by a doctor using an endoscopic procedure requiring sedation or general anesthesia. Endoscopic implantation has a 2-4% risk of complications requiring emergency removal of the capsule. Another known implantation technique involves passing the capsule through the nasal passage; however, the large size of known remote sensing capsules, which include transmitters and batteries, may result in trauma to the patient during insertion of the capsule through the nasal passage.

SUMMARY

In one aspect, the invention relates to an apparatus for measuring physiological conditions. Accordingly, in an embodiment of the invention, an apparatus for measuring a value of at least one physiological property at an internal body location of a subject is provided. The apparatus includes a sensor adapted to measure a value of a physiological property (e.g. pH, temperature, pressure, electrical impedance, etc.) at a selected internal body location. The apparatus may also include a transmitter adapted to transmit information regarding the measured value to a receiver outside of the subject without a wired connection to the receiver.

The apparatus may further include a tether and an anchor adapted to maintain an internal body location of the sensor. The anchor is adapted to attach to an externally accessible surface of the body (such as within a nasal cavity of the patient, or a body surface external to and adjacent to the nasal cavity or mouth). The tether connects the anchor disposed at a proximal end portion of the tether with the sensor disposed at a distal end portion of the tether. The relatively small diameter tether maintains a location of the sensor within the GI tract of the subject, allowing the sensor to measure the physiological property at a selected location over time while reducing discomfort associated with "pull" by the subject's organs, such as may be experienced with conventional catheters.

In another aspect, the invention relates to an instrument adapted to position a sensor assembly within the gastrointestinal tract of a patient. Accordingly, in another embodiment of the invention, an instrument for inserting and positioning a physiological sensor-transmitter assembly having a sensor with a connected tether is provided. The instrument includes an insertion section of the instrument with a diameter suitable for insertion through the nasal-gastric segment of the gastrointestinal tract of the subject. The instrument also includes a deployment section disposed at a distal end portion of the insertion section that is configured to retain the sensor with the connected tether when the instrument is in a retention state. The instrument also includes a deployment mechanism adapted to release the sensor from the deployment section in the gastrointestinal tract of the subject by changing the instrument state from a retention state to a release state.

In yet another aspect, the invention relates to a method of remotely monitoring a physiological value at a selected location within a body of a subject. In some embodiments, the method includes providing a physiological measurement sensor-transmitter assembly that has a transmitter, an anchor, a sensor, and a tether connecting the anchor and the sensor. The method also includes providing an instrument adapted to insert and position the sensor with the connected tether in a subject that has an insertion section having a proximal end portion and a distal end portion, a deployment section disposed at a distal end portion of the insertion section adapted to hold the sensor with the connected tether before deployment, and a deployment mechanism adapted to deploy the sensor from the deployment section. The method also includes inserting the distal end portion of the insertion section of the instrument through a nasal-gastric segment of a gastrointestinal tract of the subject and advancing the distal end portion of the insertion section along the gastrointestinal tract until the deployment section is positioned at the selected internal body location. The method also includes deploying the sensor with the connected tether at the selected internal body location using the deployment mechanism. The method also includes attaching the anchor to an externally accessible surface of the subject's body. The method includes withdrawing the insertion section of the instrument through the nasal-gastric segment of the subject and wirelessly receiving a signal from the transmitter including information regarding a value of a physiological property measured by the sensor at the selected internal body location for a period of time.

BRIEF DESCRIPTION OF THE DRAWINGS

FIG. 5A schematically depicts an assembly with a transmitter disposed at the anchor, according to an embodiment of the invention;

FIG. 5B schematically depicts an assembly with a transmitter disposed at the anchor, a first sensor and a second sensor, according to another embodiment of the invention;

FIG. 5C schematically depicts an assembly with a transmitter disposed at a distal end portion of the tether, according to another embodiment of the invention;

FIG. 8A depicts a side cross-sectional view of a deployment section of an instrument with a push deployment mechanism, according to an embodiment of the invention;

FIG. 8B depicts a front view of the deployment section shown in FIG. 8A;

FIG. 9A depicts a side cross-sectional view of a different embodiment of a deployment section with a push deployment mechanism, according to an alternative embodiment of the invention;

FIG. 9B depicts a front view of the deployment section shown in FIG. 9A;

FIG. 10A depicts a side cross-sectional view of a deployment section having a pull deployment mechanism, according to another embodiment of the invention;

FIG. 10B depicts a front view of the deployment section shown in FIG. 10A;

FIG. 11A depicts a side cross-sectional view of a deployment section having an air pressure deployment mechanism, according to another embodiment of the invention;

FIG. 11B depicts a front view of the deployment section shown in FIG. 11A;

FIG. 14B is a flow chart illustrating a second portion of a method of monitoring a physiological property at a selected internal body location over time that includes receiving and recording information regarding values measured by a sensor of the assembly, in accordance with an embodiment of the invention.

Figure 1:
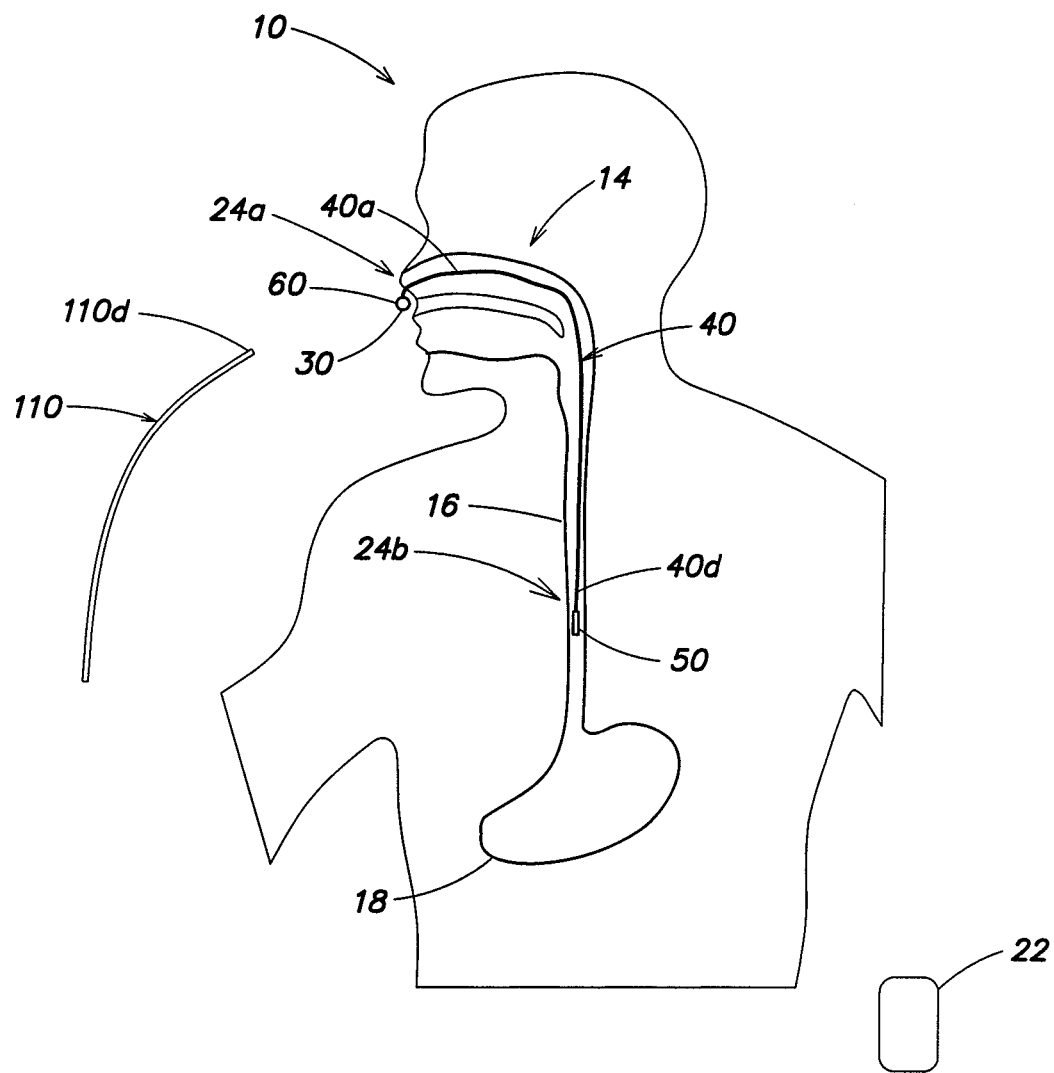
FIG. 1 schematically depicts an exemplary physiological sensor-transmitter assembly being used to measure a value of a physiological property at an internal body location of a subject and to transmit information regarding the measured value to a receiver external to the body of the subject without a wired connection, according to an embodiment of the invention.

Other advantages, novel features, and objects of the invention, and aspects and embodiments thereof, will become apparent from the following detailed description, when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment or aspect of the invention shown where illustration is not necessary to allow those of ordinary skill in the art to understand the invention.

DETAILED DESCRIPTION OF THE INVENTION

An improved physiological monitoring system is more simply and less invasively deployed. An improved monitoring system is also more comfortable to a subject and less visible while used. The inventor has appreciated that known physiological monitoring systems for the upper gastrointestinal (GI) tract that employ catheters extending from the upper GI tract through the nose and to the waist of a patient may cause the patient pain, discomfort, and self-consciousness. Systems that employ implanted remote sensing capsules involve moderately invasive implantation procedures having non-negligible complication rates and may cause trauma to a subject's nasal cavity if introduced transnasally.

Embodiments of the present invention provide a physiological sensor-transmitter assembly, an instrument adapted to insert and position a sensor of the assembly at a selected location within a subject, and a method of monitoring a physiological property at the selected location within a subject over a period of time. An exemplary physiological sensor-transmitter assembly has a sensor, an anchor adapted to attach to an externally accessible portion of the subject's body, a tether connecting the anchor and the sensor, and a transmitter. The anchor and tether restrain the sensor from moving relative to the gastrointestinal tract (GI) of the subject. The small diameter tether reduces pain and discomfort due to organ pull, relative to known large diameter catheter systems. The transmitter transmits information regarding the values measured by the sensor to a receiver without a wired connection with the receiver. Because of its small size and location either at the anchor or elsewhere along the tether, the transmitter avoids the spectacle associated with known catheter systems having the catheter exiting the nose of the subject and extending to the subject's waist. The small size of elements of the assembly and the ability to anchor the assembly at an externally accessible portion of the subject's body avoid intrusive implantation procedures that may be associated with known implanted remote capsule sensor/transmitters.

In some embodiments, a small diameter tether is used. The inventor has appreciated that a small diameter tether can significantly reduce the level of discomfort experienced by a patient for whom physiological conditions are being monitored. Use of a small diameter tether leads to the patient experiencing relatively little sensation of a foreign body in the patient's throat and/or nasal passage, which can be alarming sensation. Also, the patient experiences relatively little pulling sensation, particularly in the nasal passage, as sections of a sensor assembly, which are located in the esophagus, are pulled via peristalsis in the esophagus against the anchored portions of the assembly. Small diameter sensors may likewise be used.

Although aspects of the invention described below are described primarily in relation to measurements of physiological properties (e.g. pressure, pH level, temperature, voltage, tissue impedance, etc.) within the upper gastrointestinal tract of a human subject, such aspects are not limited to the upper gastrointestinal tract of humans, but also apply to other internal body lumens and organs of human and non-human subjects. Physiological properties that may be measured include any physiological property for which there is suitable sensor. The function and advantage of these and other embodiments of the present invention will be more fully understood from the examples described below. The following examples are intended to facilitate an understanding of aspects of the present invention and their benefits, but do not exemplify the full scope of the invention.

FIG. 1 schematically depicts an exemplary physiological sensor-transmitter assembly 24 being used to measure values of at least one physiological property (e.g. pressure, pH level, temperature, voltage, tissue impedance, etc.) at an internal body location of a subject 10 and transmit information regarding the measured values to a receiver 22 external to the body via non-wired transmission, in accordance with an embodiment of the invention. The assembly 24 includes a sensor 50 adapted to measure a value of a physiological property at a selected internal body location when the sensor 50 is positioned at the selected internal body location. Here, the internal body location is within the subject's upper GI tract. As depicted, the sensor 50 is located in the esophagus 16 of the subject.

The sensor 50 is restrained from traveling further down the GI tract of the subject 10 by an anchor 30 and a tether 40 that connects the anchor 30 with the sensor 50. The anchor 30 is adapted to attach to an externally accessible portion of a surface of the body 10. For reference purposes, when describing a path that extends from the nostril of the patient to the stomach of the patient, proximal will refer to a direction on the path toward the nostril and distal will refer to a direction on the path toward the stomach. The anchor 30 may be adapted to attach to a body location proximal to the esophagus of the subject. In some embodiments, the anchor 30 may be adapted to attach to a body location in or near the nasal cavity of the subject (as depicted). In other embodiments, the anchor 30 may be adapted to attach to a surface of the nasal cavity or to skin on the face of the subject. The tether 40 connects the anchor 30 disposed at a proximal end portion 40a of the tether with the sensor 50 disposed at a distal end portion 40d of the tether. When the anchor 30 is attached to a body location of the subject, the tether 40, which connects the anchor 30 and the sensor 50, prevents the sensor 50 from moving further along the GI tract of the subject.

The assembly 14 also includes a transmitter 60 adapted to transmit information regarding a value of a physiological property measured by the sensor to a receiver 22 located external to the body of the subject 10, without a wired connection with the receiver 22 (e.g. via a wireless radio frequency (RF) signal, via an infrared (IR) signal, etc.). The transmitter 60 may be a transmitter as known in the art or any suitable transmitter.

The receiver 22 may be attached to the subject, carried by the subject or in proximity to the subject. The receiver 22 may be inconspicuously located on or near the head of the subject, such as in a necklace, pendant or tucked behind the ear of the subject, or elsewhere on the subject. Because a location of the sensor 50 is maintained by the anchor 30 and the tether 40, the assembly 24 may transmit information regarding multiple values of a physiological parameter measured at the same internal body location over an extended period of time.

FIG. 1 also depicts an instrument 110 for inserting and positioning the sensor 50 and the connected tether 40 of the assembly 24 at a selected internal body location. The instrument is adapted to hold and retain the sensor 50 with the connected tether in a distal end portion 110d of the instrument 110 as the instrument is inserted into the subject through the naso-sinus segment. The distal end portion 110d of the instrument is advanced into the subject until the sensor 50 is positioned at the selected internal body location. The sensor 50 with the connected tether 40 is deployed and the instrument 110 is withdrawn from the subject without withdrawing the sensor 50 and the connected tether 40. Further details regarding the instrument 110 are described below with respect to FIGS. 6-12.

Many different electronic elements and electronic components that may be incorporated into a physiological sensor-transmitter assembly 24 will be collectively referred to as "electronics" herein. Such electronics may include, but are not limited to: analog to digital converters (ADCs) to convert analog voltages to digital signals, elements for signal processing, one or more batteries for powering the transmitter 60 and/or the sensor 50, receptacles to receive batteries, electrical contacts, etc. In some embodiments, portions of the electronics may be incorporated into, or integral with, the transmitter 60, the sensor 50, the tether 40, and the anchor 30. In other embodiments, the electronics may be integrated into an electronics unit separate from the transmitter 60 and the sensor 50. The electronics may be constructed using known electronics manufacturing techniques or in any other suitable way.

Although the sensor 50 is depicted at a particular location in the subject's esophagus 16, the sensor 50 may be positioned at any point along the upper gastrointestinal (GI) tract of the subject. Additionally, the assembly 24 may include more than one sensor 50, and each may be disposed at a different location of the assembly 24. Electronics associated with the sensor 50 may be disposed at different locations on the assembly 24. Additional details regarding embodiments of the sensor are described below with respect to FIGS. 4A-5F.

Although the transmitter 60 is depicted at the anchor 30 in the embodiment illustrated in FIG. 1, the transmitter may be disposed at any location on the assembly 24. In some embodiments, a transmitting element of the transmitter 60 may be spatially separated from other electronics associated with the transmitter 60. In some embodiments, the transmitter 60 is disposed at a proximal end portion of the assembly 24b. In other embodiments, the transmitter 60 is disposed at a distal end portion of the assembly 24b. In some embodiments, part of the transmitter is disposed at a proximal end portion 24a of the assembly and part of the transmitter is disposed at a distal end portion 24b of the assembly. In some embodiments, the transmitter 60 is disposed at the anchor 30, at the sensor 50, or near the sensor 50. In other embodiments, the transmitter 60 may be integrated in a same unit as the sensor 50 or integrated in a same unit as the anchor 60. The assembly 24 may include more than one transmitter 60 and each transmitter may be disposed at a different position on the assembly 24. In some embodiments, electronics may couple signals representing measurements from multiple sensors to a single transmitter which may be a multi-channel transmitter. Accordingly, the number and position of the transmitter is not critical to the invention. In other embodiments, the transmitter may be disposed at the oropharynx of the subject. Additional details regarding the transmitter and alternate embodiments of transmitters are described below with respect to FIGS. 4A, 4B and 5A-5F.

Figure 2:
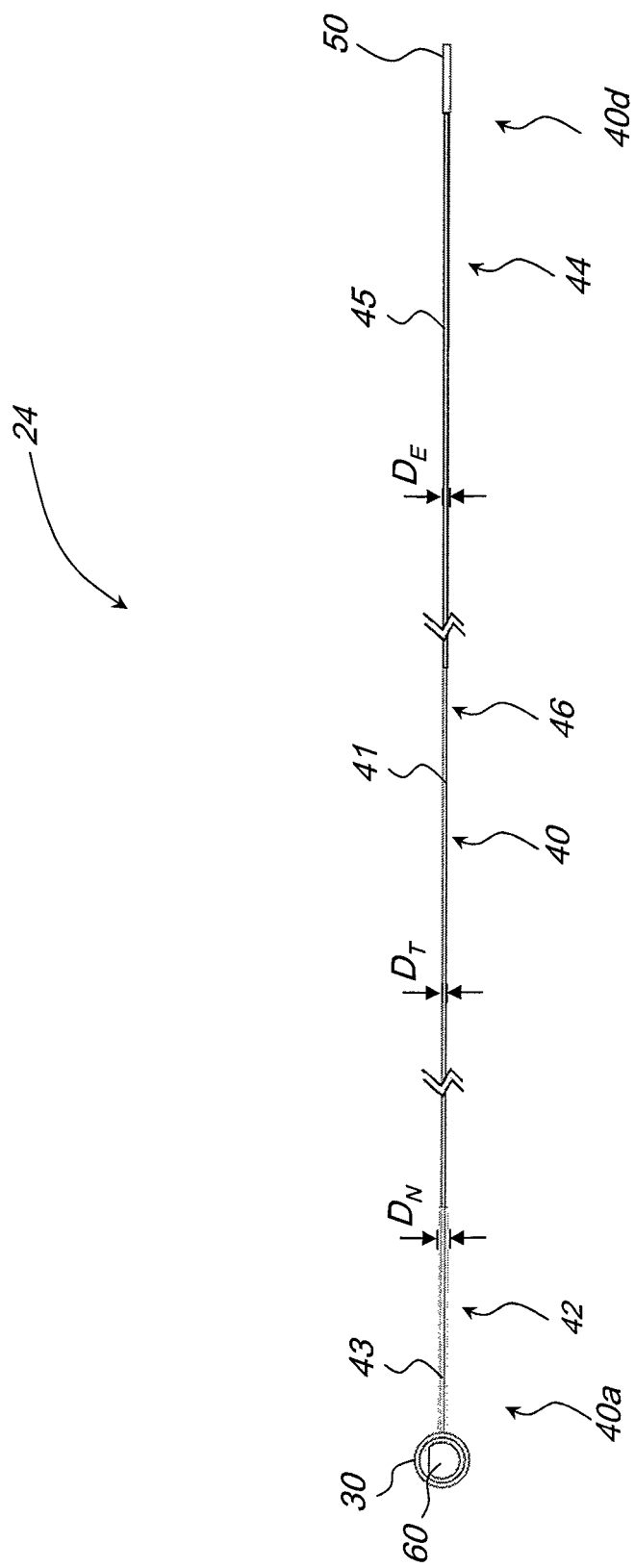
FIG. 2 schematically depicts the exemplary physiological sensor-transmitter assembly shown in FIG. 1.

An exemplary embodiment of a physiological sensor-transmitter assembly 24 for esophageal acidity monitoring is schematically depicted in FIG. 2. In the embodiment illustrated, tether 40 is active, meaning that the tether 40 is adapted to perform an additional function, such as conducting a signal, as well as maintain a position of the sensor 50. Tether 40 may include separate members to provide mechanical strength and to provide electrical conductivity. Though, in some embodiments, tether 40 may be constructed of a single member that provides both mechanical strength and electrical conductivity.

In other embodiments, a tether connected to a sensor assembly may be a passive tether, meaning that the tether is adapted to maintain a position of the sensor 50, but is not adapted to conduct a signal.

The tether 40 may have an active portion and a passive portion. As depicted, the transmitter 60 is disposed at the anchor 30, and tether 40 is depicted as an active tether that conducts a signal from the sensor 50 to the transmitter 60. An active tether 40 may include a wire 41 to conduct an electrical signal. In some embodiments, the wire may be a shielded conductor, such as a small diameter (micro) coaxial cable. Suitable materials for a conductor of the tether include, but are not limited to: copper, silver-plated copper, beryllium copper, silver-plated beryllium copper and stainless steel. Embodiments of a signal conducting tether 40 may include any signal conductors known in the art (such as a micro-coaxial cable or flex circuit) or any other suitable signal conductor. In this exemplary embodiment, the wire 41 is a micro-wire that is a micro-coaxial cable.

The tether 40 of the assembly 24 is adapted to reduce pain and discomfort of the subject during use. The tether 40 may be described as having a nasal portion 42 disposed at a proximal end portion 40a of the tether, an esophageal portion 44 disposed at a distal end portion 40d of the tether and a central portion 46 between the nasal portion 42 and the esophageal portion 44.

The nasal portion 42 may be sized to extend the length of a subject's nasal cavity, which is commonly about 4 to 8 cm. The central portion 46 may be between about 15 and about 25 cm in length and adapted to extend through the sinus and throat of the subject and into the proximal esophagus. The esophageal portion 44 may be between about 10 and about 20 cm in length. A small diameter of the tether $D_T$ may reduce pulling on the tether by organs in contact with the tether 40 and thereby reduce discomfort. In some embodiments a diameter of the tether $D_T$ for portions of the tether 40 other than the nasal portion 42 (e.g. the central portion 46 and the esophageal portion 44) is less than about 1.0 mm. In some embodiments, a diameter of the tether away from the nasal portion $D_T$ may be less than about 0.5 mm. In still other embodiments, a diameter of the tether may be between about 0.1 mm and about 0.25 mm. Several factors determine a practical lower end for a diameter of the tether $D_T$. These factors include, but are not limited to: a diameter required for a tether to have sufficient stiffness at an esophageal portion of the tether, and a total number of different signal conductors required for a signal conducting tether. As depicted, the central portion 46 of the tether 40 between the proximal end portion 40a and the distal end portion 40b of the tether is a micro-wire that is a micro-coaxial cable with a diameter $D_T$ of about 0.22 mm.

To reduce stress contact points between the tether 40 and the subject's nasal passage, the nasal portion 42 of the tether may have a nasal portion diameter $D_N$ that is large relative to a diameter $D_T$ of other portions of the tether 40. In some embodiments the nasal portion diameter $D_N$ is between about 0.5 mm and about 2.0 mm. In other embodiments, the nasal portion diameter $D_N$ is between about 1 mm and about 2 mm. For the embodiment depicted in FIG. 2, the nasal portion diameter is about 1 mm. To further reduce discomfort for the subject, the nasal portion 42 of the tether may be constructed with an outer layer of a soft material with low stiffness. Preferably, the nasal portion 42 of the tether has a soft outer layer of an elastomeric material 43. The soft outer layer may be formed of any known suitable material including, but not limited to: silicone, a thermal plastic elastomer, a flexible polyvinyl chloride (PVC), etc. As depicted, the nasal portion of the tether 42 includes the micro-wire 41 surrounded by a soft elastomeric outer tube 43 with an outer diameter of about 1 mm.

As described above, the esophageal portion 44 of the tether 40, like the central portion 46 of the tether, may have a diameter $D_E$ smaller than the nasal portion diameter $D_N$, which may reduce pull on organs via the tether 40 from esophageal and pharyngeal peristaltic action acting on the tether 40. In some embodiments the esophageal portion diameter $D_E$ may be less than about 1.0 mm. In other embodiments, the esophageal portion diameter $D_E$ may be less than about 0.5 mm. In still other embodiments, the esophageal portion diameter $D_E$ may be between about 0.1 mm and about 0.3 mm. For the depicted embodiment, the esophageal portion diameter $D_E$ is about 0.25 mm. To reduce buckling of the tether 40, the esophageal portion 44 may include an outer stiff layer 45 that is stiffer than the nasal portion 43. The stiff outer layer 45 may result in an esophageal portion diameter $D_E$ that is greater than a central portion diameter $D_T$. For this embodiment, the esophageal portion 44 includes the micro-wire 41 surrounded by a stiff outer layer 45 that increases the esophageal portion diameter $D_E$ to about 0.25 mm. The stiff outer layer 45 may include any suitable material, including, but not limited to: a polyester material and polytetrafluorethylene (PTFE) shrink tubing.

Embodiments of the tether, such as the embodiments described above, may reduce pain and discomfort to the subject when included in an assembly to connect an anchor and a sensor, whether or not the assembly includes a wireless transmitter. Such an assembly without a wireless transmitter may include a signal conductor configured to extend past the anchor to electrically connect with an inconspicuous receiver located at or near the subject's head.

Figure 3A:
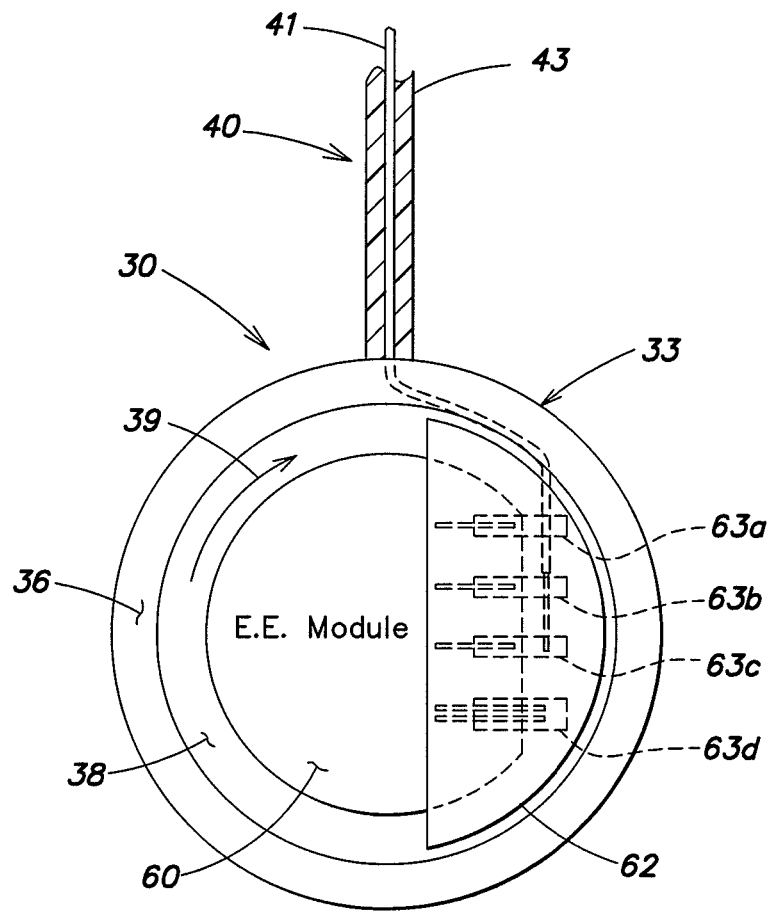
FIG. 3A schematically depicts a plan view of an anchor and a transmitter disposed at the anchor, according to an embodiment of the invention.
Figure 3B:
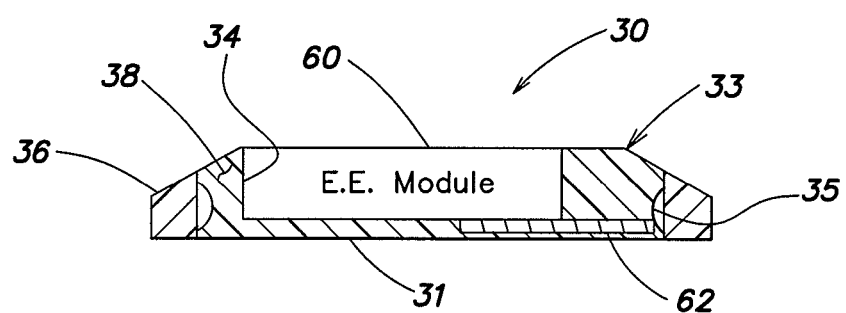
FIG. 3B schematically depicts a side cross-sectional view of the anchor and transmitter shown in FIG. 3A.

FIGS. 3A and 3B schematically depict a plan view and a side cross-sectional view of the anchor 30 and the transmitter 60 shown in FIG. 2, according to some embodiments of the invention. The anchor 30 is adapted to mechanically attach to, fasten to, or be secured at an externally accessible location of the subject 10 for retaining a position of one or more sensors 50 in the upper GI tract in resistance to axial tension caused by muscular contractions in those organs (see also FIG. 1) acting on the tether and sensors. The anchor 30 may be attached, fastened or secured to a body location of the subject 10 using any known or suitable attachment, fastening or securing technique, element or method, including but not limited to: an adhesive disposed on the anchor 30 and/or the body location, a pressure sensitive adhesive disposed on the anchor 30 and/or the body location, a layer with adhesive on both sides to be positioned between the anchor 30 and the body location (e.g. a double-sided tape), a layer with adhesive on one side to cover the anchor 30 and the body location (e.g. tape, adhesive bandage), a layer with adhesive on one side to cover a proximal end of the tether 40a, a fixture that resides within the nasal cavity that secures the anchor through mechanical constraint and may bridge the septum for mechanical stability, etc. Suitable adhesives for use with the anchor 30 include, but are not limited to: peel-release pressure-sensitive adhesives and dermatologically compatible cyanoacrylates (e.g. 2-octyl cyanoacrylate, isobutyl cyanoacrylate, etc.). In some embodiments, the anchor 30 may include an anchor plate or anchor body 33 that facilitates attachment to the body location. In other embodiments, the anchor plate or anchor body 33 may be sized and shaped to be blocked at the nares of the subject to prevent the assembly 24 from disappearing down the subject's throat if the anchor 30 inadvertently becomes unfastened or detaches from the body location.

As depicted, the anchor 30 has an anchor body 33 adapted to hold the transmitter 60, which is incorporated with other electronics into an "EE module." In this embodiment, the anchor body 33 includes a transmitter recess 34 sized and dimensioned to hold the transmitter 60 (EE module), which may optionally include signal processing circuitry or other electronics. The anchor body 33 with the transmitter recess 34 may be called a socket. A portion of the anchor 30 may be relatively compliant to facilitate removal of the transmitter 60. Suitable materials for the anchor body 30 include, but are not limited to: biocompatible rigid plastics, biocompatible semi-rigid plastics and flexible polyvinyl chloride.

The anchor 30 may be adapted to adjust a length of the tether 40. For example, the anchor body 33 may include a stationary outer ring 36 and an inner disc 38 that is rotatable relative to the stationary outer ring 36. The inner disc 38 may have a wrapping recess 35 that permits the tether 40 to be wrapped around the inner disc 38, changing a length of the tether 40. In the depicted embodiment with an anchor 30 adapted to adjust a length of the tether 40, the micro-wire 41 is free to slide within the elastomeric outer layer 43 that is affixed to the anchor 30. In embodiments where the length of the tether 40 is not adjustable, the micro-wire 41 may be affixed directly to the transmitter 60.

Due to the large number of elements that may be included in the transmitter 60 and associated electronics, a cost of a transmitter 60 and associated electronics may be a significant portion of a cost of the assembly 24. Embodiments falling within the scope of the invention include embodiments where the entire assembly 24 is disposable, embodiments where the entire assembly 24 is reusable, and embodiments where one or more elements of the assembly 24 are reusable. The anchor body 33 may be adapted to receive the transmitter 60 and the transmitter 60 may be adapted for removal from the anchor body 33 for reuse. If the transmitter 60 is reusable, then a cost of electronic components in the transmitter 60 is not born with each use, unlike the case of an implantable capsule measurement system. As depicted, an EE module including the transmitter 60 and other electronics may be removed from the anchor body 33 for reuse.

The anchor 30 and/or the transmitter 60 may include contacts adapted to electrically connect the tether 40 and the transmitter. Contacts electrically connecting the tether 40 and the transmitter 60 may be any known type of contact (e.g. soldering, wire bonding, spring contacts, etc.) or any other suitable type of contacts. The contacts may permanently electrically connect the tether 40 and the transmitter 60, or a contact may be adapted to be disconnected, such as in an embodiment with a removable transmitter 60.

The anchor body 33 includes separable electrical contacts as illustrated, and anchor body 33 includes a printed wire board (PWB) 62 for interconnecting micro-wire conductors 41 and the EE module that includes the transmitter 60. The PWB 62 includes spring contacts 63a, 63b and 63c, which connect micro-wire conductors 41 to the transmitter 60, and a double spring contact 63d, which closes a battery circuit to power the transmitter 60. The three spring contacts 63a, 63b and 63c are consistent with two sets of pH electrodes including two signal leads and a common body reference. Spring contacts 63a, 63b, 63c and 63d are adapted to connect when the transmitter 60 is inserted into the anchor body 33 and adapted to disconnect when the transmitter 60 is removed from the anchor body 33. Though, other contact arrangements are possible. For example, contacts on PWB 62 may be pads and the EE module may include compliant members that align with and make an electrical connection to those pads.

Figure 4B:
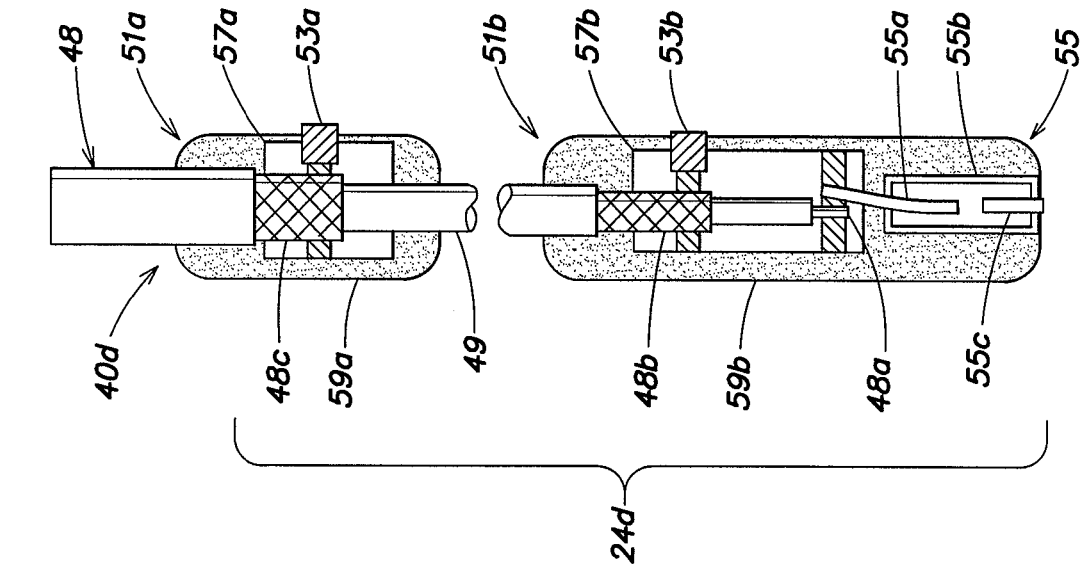
FIG. 4B schematically depicts a different embodiment of a distal end portion of the tether, a first sensor and a second sensor.
Figure 4A:
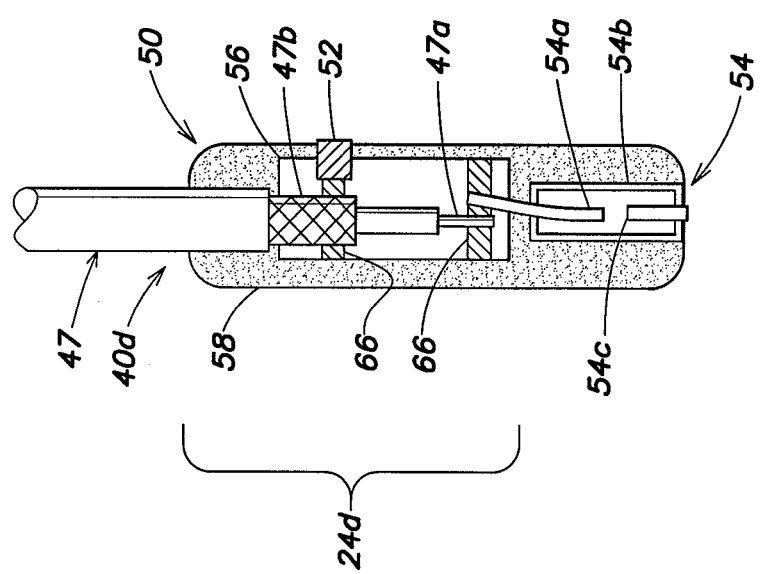
FIG. 4A schematically depicts an embodiment of a distal end portion of the tether and the sensor, according to an embodiment of the invention.

FIG. 4A schematically depicts an example of a distal end portion 24d of the assembly including the distal end portion of the tether 40d and a sensor 50, according to aspects of the invention. As used herein, a sensor 50 of a physiological sensor-transmitter assembly 24 comprises a portion of the assembly 24 at which a physiological property is detected. The sensor 50 may be passive, such as an end of an electrode, or the sensor may be active, such as a buffered pressure transducer. The sensor 50 may have associated electronics which may be disposed at any location on the assembly 24.

In the embodiment depicted in FIG. 4A, the sensor 50 is a passive sensor that measures pH by comparing a voltage at a signal electrode 52 and a voltage at a reference electrode 54. Electrodes may be made out of any suitable material by any suitable method. In one embodiment, the signal electrode 52 includes antimony and the reference electrode 54 includes silver chloride. In some embodiments, the reference electrode 54 may include a silver/silver chloride (Ag/AgCl) portion 54a that extends into a chamber 54b filled with a conducting solution such as a potassium chloride (KCl) solution. A wick 54c may extend from the chamber 54b to contact body fluids and/or body surfaces. Both the signal electrode 52 and the reference electrode 54 may be connected to a miniature printed wire board (PWB) 56, as depicted. A shielding conductor 47b of a micro-coaxial cable 47 is electrically connected to the signal electrode 52 through the PWB 56 and a central conductor 47a of the micro-coaxial cable 47 is electrically connected to the reference electrode 54 through the PWB 56. Conductors 47a, 47b of the micro-coaxial cable 47 may be electrically connected to conducting strips 66 of the PWB 56 with solder connections or by another suitable method.

A protective encapsulation material may be used to protect portions of the electrodes and/or connections between the electrodes and other elements. The signal electrode 52 and the reference electrode 54 may be partially encapsulated and the PWB 56 may be fully encapsulated by a protective electrically insulating material 58 to protect the PWB 56 and to protect exposed conducting portions of the micro-coaxial cable 47. Suitable encapsulation materials may include, but are not limited to: biocompatible epoxies and UV-light curing adhesives. Suitable biocompatible epoxies may have a very low liquid permeability and high resistance to acid and other fluids within the upper GI tract.

As depicted, a signal from the sensor 50 is conducted to the transmitter 60 located proximal to the sensor 50 along the tether 40 to the anchor 30. However, in some embodiments at least a portion of the transmitter 60 may be located at a distal portion of the assembly 24d, at least a portion of the transmitter 60 may be located at or near the sensor, and/or at least a portion of the transmitter 60 may be integrated with the sensor in a module.

FIG. 4B depicts a different embodiment of the distal end portion 24d of the assembly that includes a first sensor 51a adapted to measure a physiological condition, such as pH, at a first location in a body and a second sensor 51b adapted to measure a physiological condition, such as pH, at a second location in a body. In this embodiment, the first sensor 51a includes a first signal electrode 53a that is electrically connected to a first micro printed wire board (PWB) 57a. A distal end portion 40d of the tether includes a double coaxial micro-wire 48. An outer annular conductor 48c of the coaxial micro-wire 48 is electrically connected to the first signal electrode 53 through the first PWB 57a.

Another section 49 of the coaxial micro-wire extends from the first sensor 51a to the second sensor 51b. A middle conductor 48b of the coaxial micro-wire 48 is electrically connected to the second signal electrode 53b through a second micro printed wire board (PWB) 57b. An inner conductor 48a of the coaxial micro-wire 48 is electrically connected to the reference electrode 55 through the second PWB 57b. In this embodiment, the reference electrode 55 includes a metal portion 55a, a chamber 55b filled with a conducting fluid into which the metal portion 55a extends, and a wick 55c extending from the chamber 55b. The first PWB 57a and portions of the first signal electrode 53a may be encapsulated by a protective material 59a. The second PWB 57b, portions of the second signal electrode 53b and portions of the reference electrode 55 may be encapsulated by a protective electrically insulating material 59b.

Embodiments of the invention may include active pH sensors, such as ion-sensitive field effect transistors (ISFETs). Active pH sensors may be electrically connected to micro-coaxial signal conducting tethers using PWBs. Due to the relatively simple interconnection geometry in relation to the coaxial micro-wire 47, 48, the embodiments shown in FIGS. 4A and 4B are suitable for automated or semi-automated production. Although embodiments depicted in FIGS. 4A and 4B include coaxial cable signal conductors, embodiments of the present invention may include any suitable type of conductors for signal conducting tethers including, but not limited to: non-coaxial conductors grouped in a shielded or non-shielded cable, a combination of co-axial and non-coaxial conductors, etc.

Figure 5F:
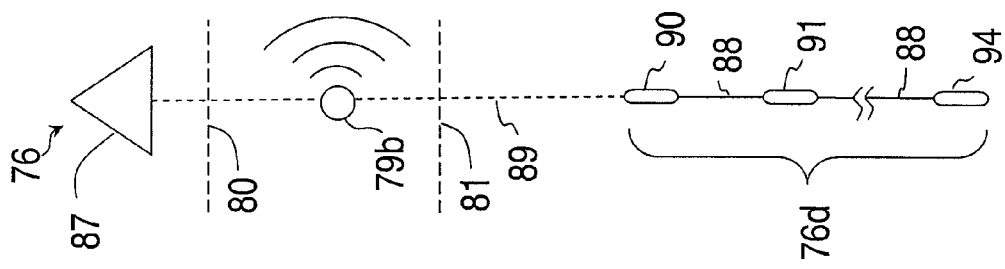
FIG. 5F schematically depicts an assembly having a first sensor, a first transmitter disposed proximal to the first sensor, a second sensor and a third sensor, according to another embodiment of the invention.

Embodiments of a physiological sensor-transmitter assembly may have many different configurations, according to aspects of the invention. The examples of configurations presented herein are merely illustrative and not an exhaustive representation of all configurations of assemblies falling within the scope of the invention. FIGS. 5A to 5F schematically represent some possible configurations of a physiological sensor-transmitter assembly. In each figure, elements above line 80 are adapted to be positioned in the nasal cavity or other externally accessible part of the body and elements below line 80 are adapted to be positioned distal to the nasal cavity. In FIG. 5F, elements above line 81 are adapted to be positioned proximal to the esophagus, and elements between lines 80 and 81 are adapted to be positioned between the nasal cavity and the esophagus (e.g. at the oropharynx).

Assembly 71 and assembly 72, depicted in FIGS. 5A and 5B respectively, both include a transmitter 77 disposed at or near an anchor 86, and a signal conducting tether 88 that conducts a signal from the a first sensor 90 to the transmitter 77. Assembly 72 includes a second sensor 91 disposed distal to the first sensor 90 at a distal end portion 72d of the assembly. A signal conducting tether 88 connects the second sensor 91 with the transmitter 77. In this embodiment, the transmitter 77 is a multi-channel transmitter because it is adapted to transmit information regarding a signal from the first sensor 90 and information regarding a signal from the second sensor 91. Embodiments of the invention, which include multiple sensors, may be referred to as multi-channel assemblies.

In assembly 73 depicted in FIG. 5C, a transmitter 78 is disposed at a distal end portion 73d of the assembly, and specifically at or near a first sensor 92. A passive tether 89 may connect an anchor 87 with a distal end portion 73d of the assembly because a signal conducting tether is not necessary between the distal end portion 73 of the assembly and the anchor 87 if no electronics are present in the anchor 87. In other embodiments at least a portion of the transmitter 78 may be in an integral unit with the first sensor 92 and/or at least a portion of the transmitter 78 may be near the first sensor 92. Although the transmitter 78 is shown at a same location on the assembly 73 as the first sensor 92, this positioning is not required. In other embodiments at least a portion of the transmitter may be proximal to the first sensor 92 and/or at least a portion of the transmitter may be distal to the first sensor 92.

Figure 5E:
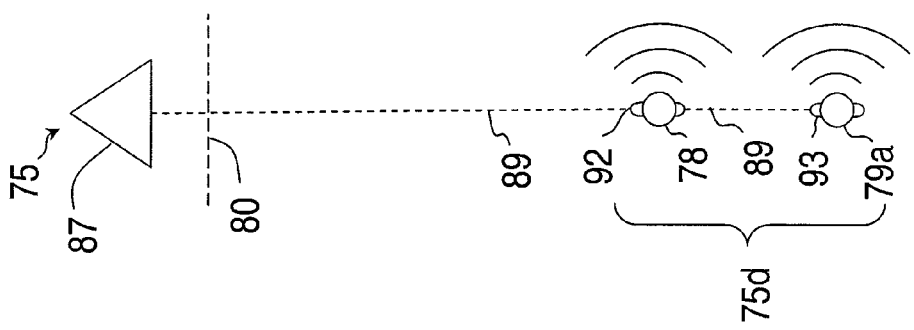
FIG. 5E schematically depicts an assembly having a first sensor, a first transmitter disposed at the first sensor, a second sensor, and a second transmitter disposed at the second sensor, according to another embodiment of the invention.
Figure 5D:
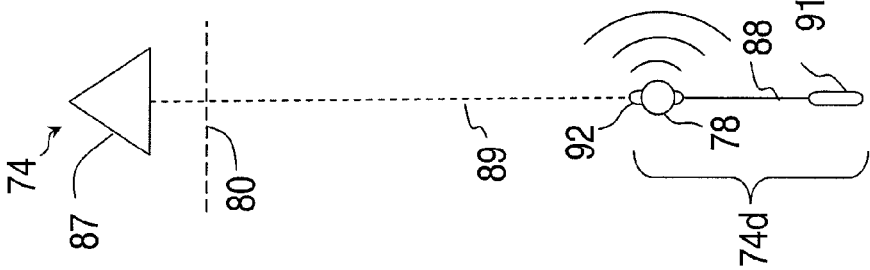
FIG. 5D schematically depicts an assembly having a first sensor, a second sensor and a transmitter disposed at the first sensor, according to another embodiment of the invention.

In assembly 74, depicted in FIG. 5D, a second sensor 91 as well as the transmitter 78 and the first sensor 92 are disposed at a distal end portion 74d of the assembly. As depicted, the second sensor 91 is connected to the transmitter 78 by an active signal conducting tether 88. The multi-channel transmitter 78 transmits information regarding a signal from the first sensor 91 and information regarding a signal from the second sensor 92. Although the transmitter 78 is depicted at the first sensor 92, in other embodiments at least a portion of the transmitter 78 may be at or near the second transmitter 91. In other embodiments at least a portion of the transmitter may be located proximal to the first sensor 92, or located between the first sensor 92 and the second sensor 94.

In assembly 75 depicted in FIG. 5E, information regarding measurements from the first sensor 92 is transmitted by the first transmitter 78 and information regarding measurements from the second sensor 93 is transmitted by a second transmitter 79a. An active signal conducting tether is not required between the first transmitter 78 and the second transmitter 79a. Although the second transmitter 79a is depicted at the second sensor 93, in other embodiments at least a portion of the second transmitter may be located at or near the first sensor 92, between the first sensor 92 and the second sensor 93, at or near the first transmitter 78 or at or near the anchor 87.

Assembly 76, depicted in FIG. 5F, includes a first multi-channel transmitter 79b to transmit information regarding measurements from a first sensor 90, a second sensor 91 and a third sensor 94 disposed at a distal end of the assembly 76d. In FIG. 5F line 80 indicates a distal edge of the nasal cavity and line 81 indicates a proximal edge of the esophagus. Transmitter 79b may be disposed between the nasal cavity and the esophagus, as depicted. In an embodiment of the invention, the transmitter 79b may be disposed in the oropharynx (or oral pharynx) which is located between the nasal cavity and the esophagus. The oropharynx has reduced sensation of foreign objects relative to other regions of the pharynx due in part to the absence of muscular contractile activity, which can squeeze such an object resulting in elevated contact pressures. Thus, positioning the relatively large sized transmitter 79b at the oropharynx and behind the soft palate may ensure a relatively low level of discomfort for the patient.

Although the configurations shown in FIGS. 5A through 5F depict up to three sensors and two transmitters for each assembly, assemblies with many more sensors and/or transmitters also may be constructed. In some embodiments, the first transmitter 78 may be of a different type than the second transmitter 79a. In other embodiments, the first transmitter 78 may be of a same type as the second transmitter 79a. In some embodiments, the first sensor 92 and the second sensor 93 may measure the same physiological property at different locations. In other embodiments, the first sensor 92 and the second sensor 93 may measure the different physiological properties at the same location or at different locations.

Figure 6A:
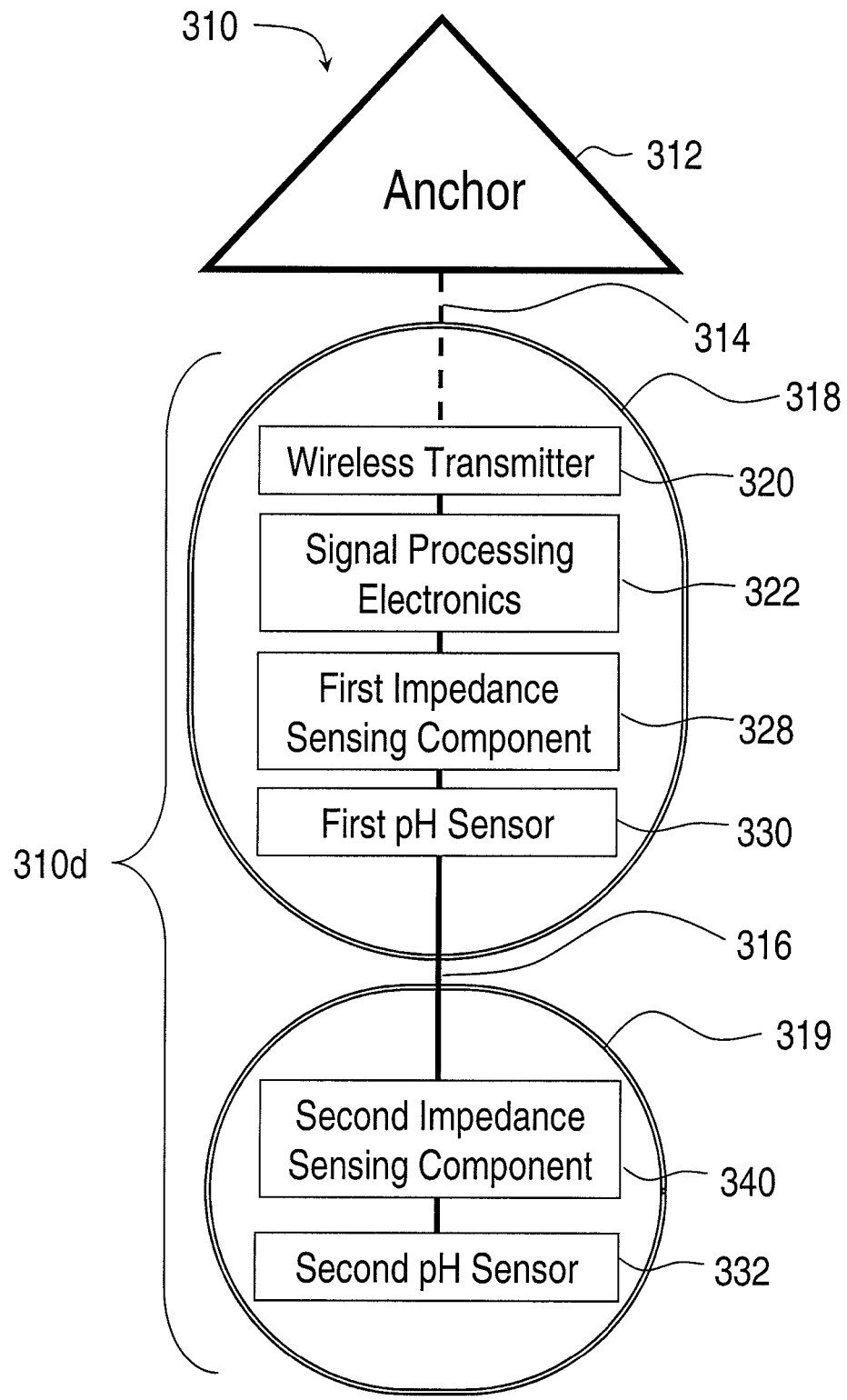
FIG. 6A schematically represents an assembly having a first pH sensor, a second pH sensor, a first impedance sensing component and a second impedance sensing component, according to an embodiment of the invention.

Intraluminal impedance monitoring, which detects the occurrence of changes in a resistance to electrical current across adjacent electrodes positioned in a serial manner along an axial length in the GI tract, aids in differentiating between antegrade and retrograde bolus transit of both liquid and gas in the GI tract. Because impedance sensing components do not identify an acid content at a location, pH sensors are often used along with impedance sensing components. FIG. 6A schematically represents an assembly 310 that includes sensors that measure two different types of physiological properties, acidity and electrical resistance, at a same location for each of two different groups located at two different locations on the tether, according to another embodiment of the invention.

Assembly 310 includes a first pH sensor 330, a second pH sensor 332, a first impendence sensing component 328 and a second impedance sensing component 340 An anchor 312 is connected with a distal end portion of the assembly 310d by a passive tether 314. A first group of elements 318 at the distal end portion of the assembly 310d includes a wireless transmitter 320, signal processing electronics 322, the first impedance sensing component 328 and the first pH sensor 330. A signal conducting tether 316 conducts the first group of elements 318 with a second group of elements 319 that includes the second impedance sensing component 340 and the second pH sensor 332. The first group of components 318 measures pH and impedance at a first location and the second group of components 319 measures pH and impedance at a second location.

Figure 6B:
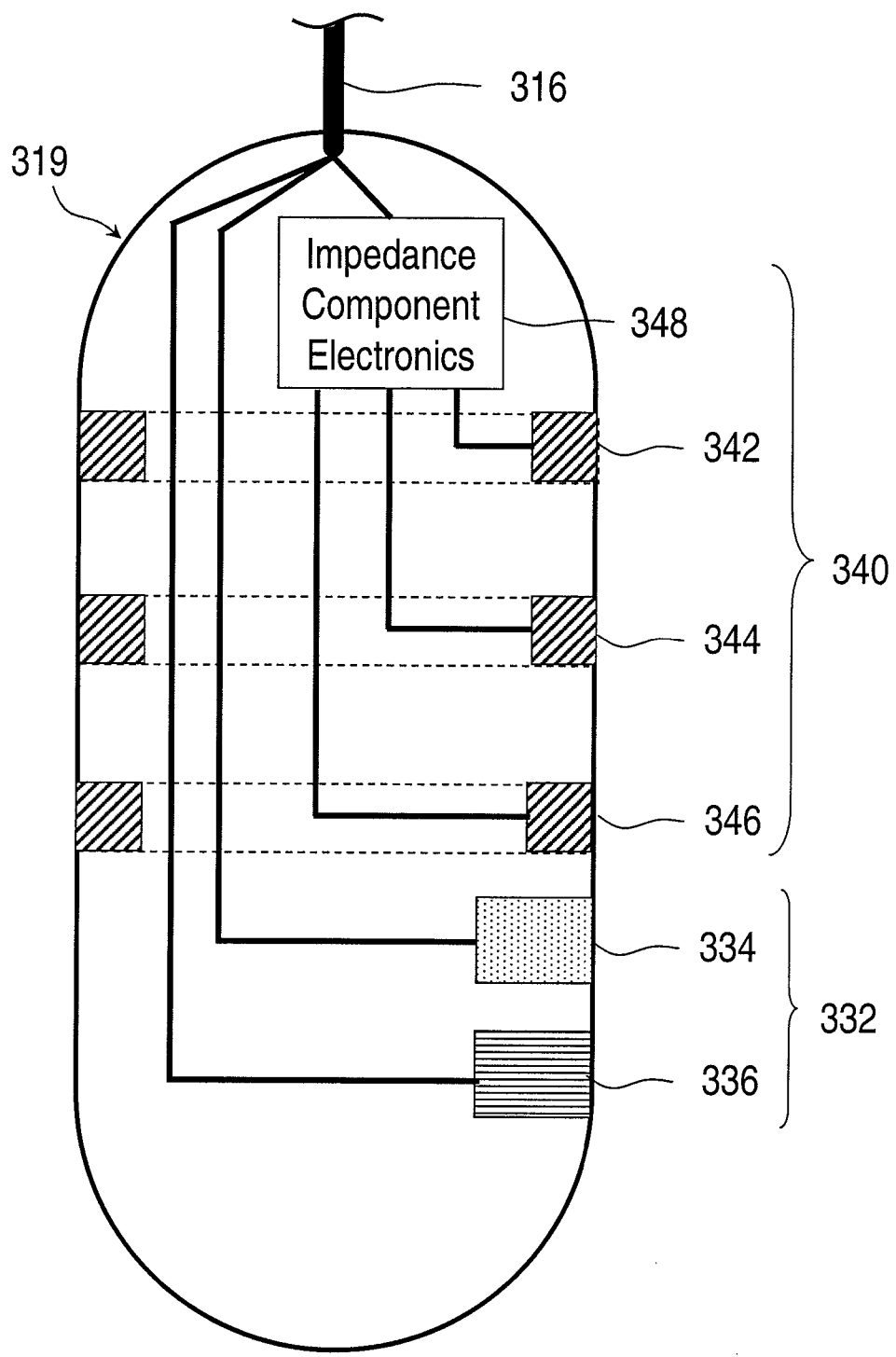
FIG. 6B schematically represents further details of the second pH sensor and the second impedance sensing component shown in FIG. 6A, according to another embodiment of the invention.

FIG. 6B schematically represents the second group of elements 319. The impedance sensing component 340 includes a first electrode 342 a second electrode 344 and a third electrode 346. Impedance electrodes may be shaped like rings (as indicated by dotted lines in the figure) that located along a common axis. Impedance component electronics 348 are configured to determine an electrical impedance between the first electrode 342 and the second electrode 344, and to determine an electrical impedance between the second electrode 344 and the third electrode 346. Because impedance may be determined for two locations simultaneously within a body lumen, the impedance sensing component can be used for multi-channel impedance measurements. The second group of elements 319 also includes a reference electrode 334 and a signal electrode 336 that form the second pH sensor 332. Signals from the impedance sensing component 340 and the second pH sensor 332 are then conducted to the rest of the assembly 310 by the active conducting tether 316.

Figure 7:
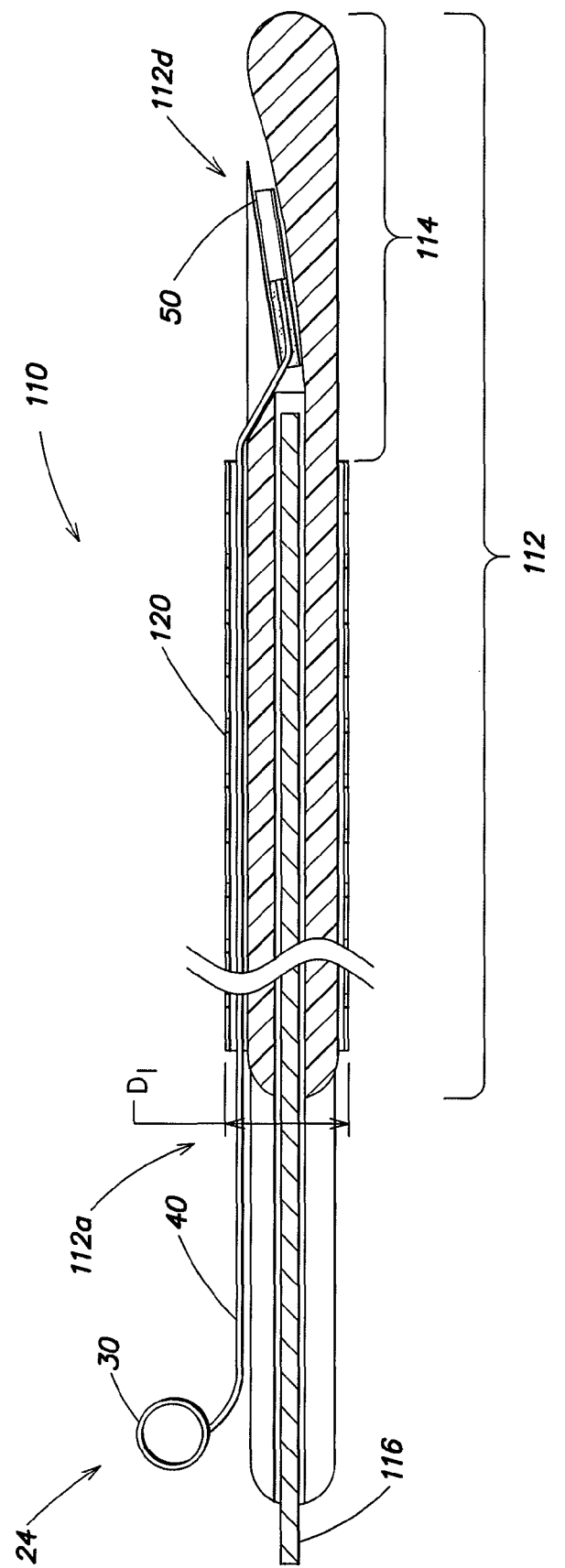
FIG. 7 schematically depicts an instrument for inserting and positioning a sensor of an assembly with a connected tether, in accordance with an embodiment of the present invention.

FIG. 7 schematically depicts an instrument 110 for inserting and positioning the sensor 50 and connected tether 40 of the physiological sensor-transmitter assembly 24 in a chosen location within a subject, in accordance with another embodiment of the invention. Note that dimensions in the figure are exaggerated for illustrative purposes. Although instrument 110 is described herein with respect to an exemplary physiological sensor-transmitter assembly 24, instrument 110 is not limited to use with an assembly 24 having a sensor 50, an anchor 30, a tether 40 and a transmitter 60. Instrument 110 may be used to insert and position assemblies having fewer elements, more elements or different elements than those described herein, (e.g. an assembly having a sensor 50 and a tether 40 with an anchor 30, but not a transmitter 60; an assembly having a sensor 50 and a transmitter 60, but not a tether, etc.)

The instrument 110, which may also be referred to as an "introducer," provides a mechanism for securing the sensor 50 and connected tether 40 during insertion, and provides a mechanism for deployment of the sensor 50 and connected tether 40 after insertion. The instrument 110 has an insertion section 112 with a diameter $D_I$ suitable for insertion through the nasal-gastric segment of the GI tract of the subject. For one embodiment of the invention, a diameter of the instrument section $D_I$ between about 1 mm and about 5 mm. The insertion section 112 must be of sufficient length to span from the nares (nasal cavity) of the subject to the desired location in the GI tract of the subject. A deployment section 114 is disposed at a distal end portion 112*d* of the insertion section. The deployment section 114 is configured to retain the sensor 50 of the assembly when the instrument 110 is in a retention state, as depicted. An embodiment of the instrument 110 may include a removable outer sleeve 120 that contains the tether 40 during insertion of the instrument 110. The removable outer sleeve 120 may have perforations to aid in removal of the outer sleeve 120 after insertion of the instrument 110 and before deployment of the sensor 50 or withdrawal of the instrument 110. The instrument 110 also includes a deployment mechanism 116 adapted to release the sensor 50 from the deployment section 114 of the instrument 110 upon changing from a retention state to a release state. FIGS. 7 through 11B depicts various embodiments of the deployment section 114.

FIGS. 8A and 8B schematically depict a side cross-sectional view and a front view respectively, of an embodiment of the deployment section 114 of the instrument 110 having a push deployment mechanism. For some embodiments, the sensor 50 is retained within a lumen-shaped receptacle 122 in the deployment section 114, as illustrated by the side cross-sectional view of FIG. 8A. The tether 40 may be contained by a removable outer layer 120 as depicted. The deployment section 114 may include a slit opening 115 that allows the tether 40 to exit the receptacle 122 and extend along an outer surface of the deployment section 114. The deployment mechanism includes an elongate push element 117, such as a push rod, that extends through the insertion section 112. After the outer layer 120 is removed, the instrument 110 may be activated by exerting a force on the elongate push element 117 as indicated by arrow 118. The elongate push element 117 in turn exerts a force on the sensor 50 to move the sensor 50 out of the lumen 122, thereby deploying the sensor 50 as indicated by arrow 119.

The deployment section 114 may also include a temporary restraining element 124 adapted to prevent withdrawal of the sensor 50 during withdrawal of the instrument 110. Some embodiments of a temporary restraining element 124 include an expandable drag-inducing material. When the sensor 50 is deployed from the deployment section 114, the temporary restraining element 124 is also expelled and separates from the deployment section 114, according to an embodiment of the invention. The temporary restraining element 124 may be adapted to expand or swell after exiting the deployment section 114. The swollen temporary restraining element 124 has high drag that may impede a motion of the sensor 50 up the GI tract as the instrument 110 is withdrawn. The temporary restraining element 124 may be attached to the sensor 50 and/or tether 40, or the temporary restraining element 124 may not be attached to either. Ideally, the temporary restraining element 124 dissolves after the instrument 110 is withdrawn. In some embodiments, the temporary restraining element 124 may include glucose, fructose, gelatin, cellulose or other paper-based fibers in a "cotton-candy like" or "tissue paper like" consistency that dissolve in water or saliva.

FIGS. 9A and 9B schematically depict a side cross-sectional view and a front view of an embodiment of a deployment section 128 that includes a different push deployment mechanism. Similar to the embodiment depicted in FIGS. 8A and 8B, the elongate push element 117 is adapted to exert a force on the sensor 50. However, in this embodiment depicted in FIGS. 9A and 9B, a portion of the tether 40 is located distal relative to the sensor 50, and the temporary restraining element 124 is also located distal relative to the sensor 50. Additionally, a receptacle 130 holding the sensor 50 and the temporary restraining element 124 is configured to lie parallel to the deployment section 128. In this embodiment of the deployment section 128, the force on the sensor 50 deploys the sensor 50 in a reversed orientation as indicated by arrow 132.

In some embodiments, an introducer as illustrated in FIGS. 9A and 9B may be implemented without a separate restraining element 124 and push mechanism. Alternatively or additionally, outer layer 120 may be omitted. In some scenarios, a simple tubular structure may be used as an introducer. In those scenarios, an introducer may be formed from a tube. A sensor, such as sensor 50 (FIG. 9A), may be inserted into the tip of the tube. A tether, such as tether 40, attached to the sensor, may run along an exterior surface of the tube, as illustrated in FIG. 9A. By maintaining a suitable tension on the tether, the sensor will be held in the tip as the tube is inserted. Once the sensor is positioned, the tube could be withdrawn, leaving the sensor in a desired location.

An embodiment of the deployment section 134 depicted in a side-cross sectional view in FIG. 10A and in a front view in FIG. 10B is adapted for a pull deployment mechanism. The deployment section 134 includes a lumen shaped receptacle 136 adapted to hold the sensor 50 and the temporary restraining element 124. The tether 40, which is attached to the sensor 50, exits the receptacle 136 through an opening 137 of the receptacle. To deploy the sensor 50, the outer layer 120 is removed and a force is exerted on the tether 40 as indicated by arrow 138, which pulls the sensor 50 out of the deployment section 134 through the receptacle opening 137.

Another embodiment of a deployment section 140 depicted in FIGS. 11A and 11B is similar in configuration to the deployment section 128 depicted in FIGS. 9A and 9B. However, in this embodiment, the deployment mechanism uses fluid pressure (e.g. gas pressure or liquid pressure) to exert a force to deploy the sensor 50 instead of an elongate push element 117. The deployment section 140 includes a fluid conduit 142 extending from a proximal end portion 112*a* of the insertion section to the deployment section 140. The fluid conduit 142 is adapted to conduct a fluid (gas or liquid) as indicated by arrow 144 that exerts a fluid force on the sensor portion 50 to push the assembly portion 50 from the deployment section 140. A receptacle 142*r* that holds the sensor 50 may be a portion of the fluid conduit 142 as depicted.

Figure 12A:
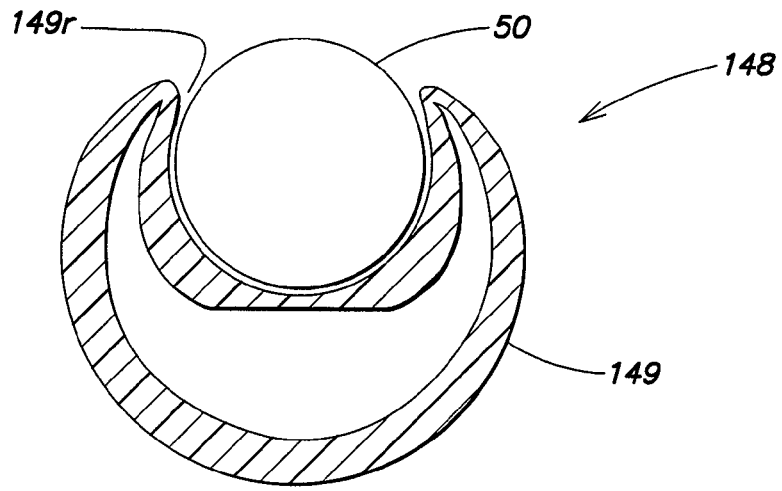
FIG. 12A depicts an axial cross-sectional view of a deployment section of an instrument having an inflatable portion in a retaining state, according to another embodiment of the invention.
Figure 12B:
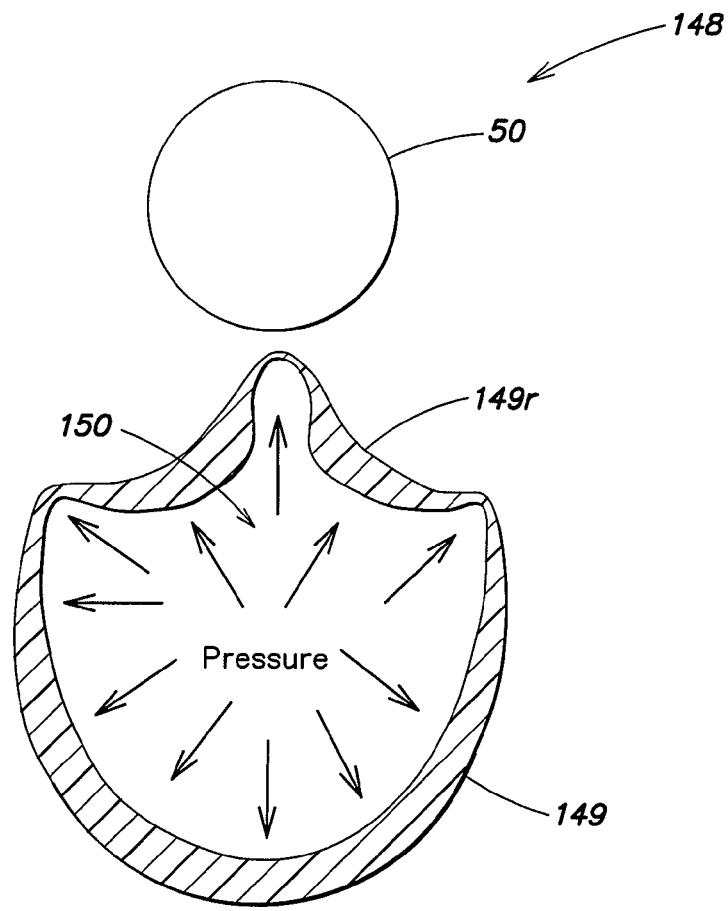
FIG. 12B depicts a cross-sectional view of the deployment section of FIG. 12A, in a release state.

A different embodiment of the deployment section 148 includes an inflatable portion 149 is depicted in FIGS. 12A and 12B. In an uninflated state, the inflatable portion 149 has a recess 149*r* that holds and retains the sensor 50, as depicted in axial cross-section in FIG. 12A. Adding an inflation fluid 150 (i.e. liquid or gas) under pressure to the inflatable portion 149 changes a configuration of the recess 149*r* so that it is no longer shaped to hold the sensor 50, thereby deploying the sensor 50 as depicted in FIG. 12B.

Figure 13:
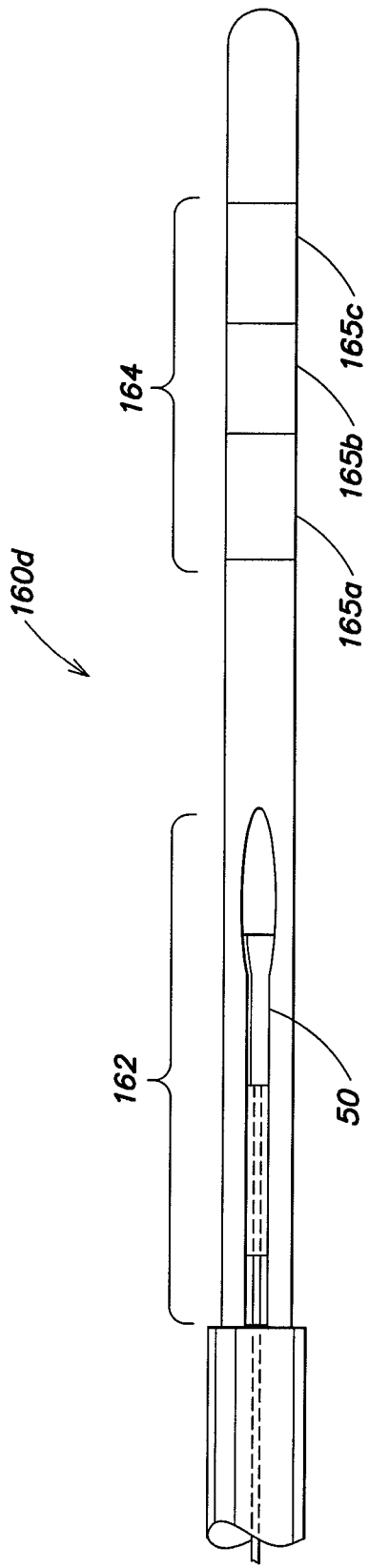
FIG. 13 schematically depicts a distal end portion of an insertion section of an instrument having instrument sensors adapted to determine a location of the deployment section, according to another embodiment of the invention.

In addition to different embodiments of the deployment section and different deployment mechanisms, an exemplary instrument may include one or more instrument sensors for determining a location of the sensor 50 of an assembly within a subject. Such an instrument that incorporates location sensing elements may be referred to as an "active introducer." FIG. 13 depicts a distal end portion 160*d* of an instrument having a deployment section 162 and pressure transduction section 164 that aids in determining a location of a distal end portion of the instrument. The pressure transduction section 164 comprises one or more sensing elements 165 *a*, *b*, *c*, disposed axially along the pressure transduction section 164. Variations in pressure within the esophagus can be correlated with a position relative to certain anatomical landmarks such as the lower and upper esophageal sphincters. Thus, measurements of pressure at a pressure transduction section 164 provide information regarding a position of a deployment section 162 of the instrument. Sensing elements 165*a*, *b*, *c* may be similar in construction to pressure transduction sensors incorporated in the Motility Visualization System (MVS) catheter produced by Sierra Scientific Instruments Inc., and described in co-pending patent application Ser. No. 10/961,981, entitled "High Resolution Solid State Pressure Sensor." When an active introducer embodiment of the instrument is used to insert and position a physiological sensing transmitting assembly for esophageal pH testing, a separate manometry test to locate the sphincters prior to insertion and final positioning of the assembly sensor may be avoided.

Figure 14A:
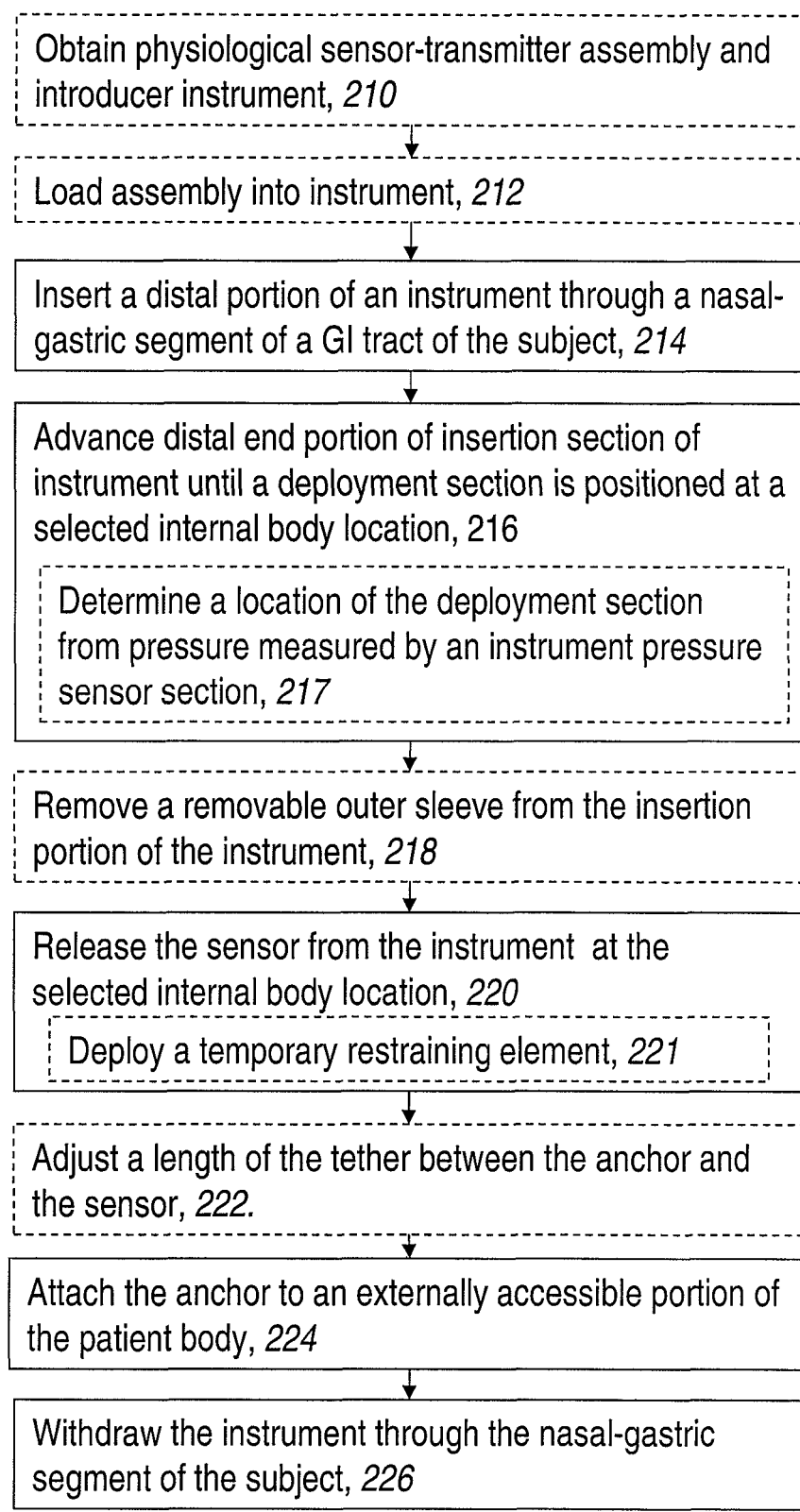
FIG. 14A is a flow chart illustrating a first portion of a method of monitoring a physiological property at a selected internal body location over time that includes inserting and positioning a physiological sensor-transmitter assembly, in accordance with an embodiment of the invention.

Another embodiment of the invention provides a method of remotely monitoring a physiological value at a selected location within a body of a subject. Although an exemplary method may be performed with many different embodiments of physiological sensor assemblies and introducer instruments, an embodiment of the method will be described with reference to the physiological sensor-transmitter assembly 24 depicted in FIG. 2, the introducer instrument 110 depicted in FIG. 7, deployment section 114 depicted in FIGS. 8A and 8B and a pressure transduction section 164 as depicted in FIG. 13, solely for illustrative purposes. The method of remotely monitoring a physiological value at a selected location within a body of a subject may be sub-divided into two different methods: inserting and positioning the physiological sensor-transmitter assembly 24 within a subject (method 200*a*), and recording information regarding measured values of the physiological property over a period of time (method 200*b*). In FIGS. 14A and 14B, dotted boxes indicate steps that may be included in different embodiments of the invention.

FIG. 14A is a flow chart illustrating a method 200*a* of inserting and positioning a physiological sensor within the gastrointestinal tract of a subject. In the embodiment illustrated, the sensor is a physiological sensor-transmitter assembly 24 as illustrated in FIG. 7. However, any suitable type of sensor may be positioned, including a sensor without a corresponding transmitter or a multi-sensor assembly.

In accordance with the illustrated method, initially a physiological sensor-transmitter assembly 24 and an introducer instrument are provided (step 210). The assembly 24 has a transmitter 60, an anchor 30, a sensor 50, and a tether 40 that connects the sensor 50 and the anchor 60. The introducer instrument 110 has an insertion section 112, a deployment section 114, and a deployment mechanism 116. The assembly 24 may be loaded into the instrument (step 212), or conversely the assembly 24 may be pre-loaded into the instrument 110 when obtained. A distal end portion 112*d* of an insertion section of the instrument is inserted into the subject through a nasal-gastric segment of the GI tract (step 214). The distal end portion 112*d* of the insertion section is advanced until the deployment section 114 of the insertion section is at a selected internal body location (step 216). If the introducer is an "active introducer" then a location of the deployment section 114 may be determined from measurements of pressure made by one or more sensor elements 165*a*, 165*b*, 165*c* of the instrument 110 to guide proper placement of the sensor 50 relative to an upper esophageal sphincter and a lower esophageal sphincter (step 217). The insertion section 112 may be advanced continuously or advanced in steps with a determination of a position of deployment 114 section between each step.

If the insertion section 112 of the instrument has a removable outer layer 120, then the outer layer 120 may be removed after the deployment section 114 is positioned at the selected internal body location (step 218). The sensor 50 with the connected tether 40 is deployed at the selected internal body location (step 220). Different configurations of deployment sections using different deployment mechanisms are described above with respect to FIGS. 7A thorough 11B. A temporary restraining element 124 may also be deployed (step 221). A length of the tether 40 may be adjusted by any suitable means (step 222) including wrapping an inner wire 41 of the tether 40 around a part of the anchor 38 as described above with respect to FIGS. 3A and 3B.

The anchor 30 is attached to an externally accessible surface of the subject's body (step 224). Examples of suitable locations for attachment of the anchor are described above. The anchor 30 may be attached using any suitable technique or method. Suitable attachment methods are described above. The insertion section 112 of the instrument is then withdrawn through the nasal-gastric segment of the subject (step 226).

After the physiological sensor-transmitter assembly is positioned in the subject, physiological properties measured at location are monitored over time (method 200*b*), then the assembly 24 may be removed from the subject as depicted by the flowchart of FIG. 14B. First a signal from the transmitter 60, including information regarding values of a physiological property measured at the selected internal body location over time, is wirelessly received at a receiver 22 (step 228). The receiver 22 may be attached to the subject, carried by the subject or in proximity to the subject. The received signal is recorded 230 in the receiver 22 or in another unit. The recorded signal may be transferred to an analysis and display device, such as a computer, (step 231). The received signal may be analyzed (step 234). Information from the received signal may be displayed (step 236). After monitoring is complete, the assembly 24 may be removed from the subject 240.

In vivo Testing of a Mechanical Model of the Assembly

The embodiment of the physiological sensor-transmitter assembly 24 shown in FIGS. 2 and 3 was built in a mechanical prototype, along with a prototype applicator, and tested in vivo in a series of three 24 hour ambulatory tests. In these tests, the subject went about normal daily activities including, unaltered meals, strenuous physical activities, and sleep, and only very minor discomfort was reported. A small "Band-Aid" type cover of 1.4 cm diameter was placed over the anchor to make it inconspicuous and the subject reported no reluctance to join social activities. Other embodiments were tested including an anchor style that filled the nostril. This was reported to cause noticeable discomfort, but one that straddles the septum and was positioned toward the anterior/superior end (toward the tip of the nose), was reported to have little discomfort and was made inconspicuous by use of a transparent element that bridged the septum. For comparison purposes, the subject was intubated for a 2 hour period with a 2.5 mm silicone tube representing a known pH catheter and reported the discomfort to be substantially greater.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

As used herein, "plurality" means two or more.

As used herein, a "set" of items may include one or more of such items.

As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, shall be closed or semi-closed transitional phrases, as set forth, with respect to claims, in the United States Patent Office Manual of Patent Examining Procedures (Original Eighth Edition, August 2001), Section 2111.03

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An instrument for inserting and positioning a sensor-transmitter assembly in a body of a subject, the instrument comprising:
   an insertion section insertable through the nasal-gastric segment of the gastrointestinal tract of a subject;
   a deployment section disposed at a distal end portion of the insertion section, the deployment section having therein a lumen shaped receptacle retaining a sensor;
   an elongate push rod extending through and slidable in the insertion section to push the sensor out of the lumen shaped receptacle in the gastrointestinal tract of the subject; and
   a removable outer sleeve encircling the insertion section and containing a tether connected to the sensor between at least the insertion section and the removable outer sleeve.

2. The instrument of claim 1, further comprising
   at least one sensor disposed at the insertion section of the instrument for determining a location of the deployment section within the subject.

3. The instrument of claim 2, wherein the at least one sensor is a pressure sensor fixedly mounted in an exterior wall of the instrument.

4. The instrument of claim 1, further comprising a temporary retaining device disposed at the deployment section of the instrument adapted to maintain a position of the sensor after deployment as the insertion section of the instrument is withdrawn from the subject.

5. The instrument of claim 4, wherein the temporary retaining device comprises a body of expandable material adapted to expand and separate from the insertion section upon deployment within the subject; and wherein the expandable material is adapted to dissolve in the subject.

6. The instrument of claim 1, wherein:
   the removable outer sleeve comprises perforations to aid in removal.

7. The instrument of claim 1, wherein the tether is outside the insertion section.

8. The instrument of claim 1, wherein the deployment section comprises a slit configured to enable the tether, attached to the sensor in the receptacle, to extend from the receptacle to an outer surface of the insertion section.

9. The instrument of claim 1, wherein the insertion section comprises an opening into the deployment section.

10. The instrument of claim 1, wherein a diameter of the insertion section is between 1 and 5 mm.

11. The instrument of claim 1, wherein the tether extends along the length of the insertion section from a location at a first end adjacent the deployment section to a location adjacent an opposing end of the insertion section.

12. An instrument for inserting and positioning a sensor-transmitter assembly in a body of a subject, the instrument comprising:
    an insertion section insertable through the nasal-gastric segment of the gastrointestinal tract of a subject;
    a deployment section disposed at a distal end portion of the insertion section, the deployment section having therein a lumen shaped receptacle retaining a sensor;
    an elongate push rod extending through and slidable in the insertion section to push the sensor out of the lumen shaped receptacle in the gastrointestinal tract of the subject; and
    a removable outer sleeve encircling the insertion section and containing a tether connected to the sensor, wherein the tether is outside the insertion section.

13. The instrument of claim 12, wherein:
    the removable outer sleeve comprises perforations to aid in removal.

14. The instrument of claim 12, wherein the deployment section comprises a slit configured to enable the tether, attached to the sensor in the receptacle, to extend from the receptacle to an outer surface of the insertion section.

15. The instrument of claim 12, wherein the insertion section comprises an opening into the deployment section.

16. The instrument of claim 12, wherein a diameter of the insertion section is between 1 and 5 mm.

17. The instrument of claim 12, wherein the tether extends along the length of the insertion section from a location at a first end adjacent the deployment section to a location adjacent an opposing end of the insertion section.

18. The instrument of claim 12, wherein the tether comprises an electrically conductive member.

19. The instrument of claim 18, further comprising:
    a transmitter connected to the sensor through the tether and adapted to transmit information regarding a value measured with the sensor to a receiver located external to the body of the subject.

* * * * *